US009409041B2

(12) United States Patent
Fedewa et al.

(10) Patent No.: US 9,409,041 B2
(45) Date of Patent: Aug. 9, 2016

(54) METHOD AND APPARATUS FOR THE TREATMENT OF TISSUE

(76) Inventors: Russell J. Fedewa, Indianapolis, IN (US); Toyoaki Uchida, Kanagawa Prefecture (JP); Narendra T. Sanghvi, Indianapolis, IN (US); Roy F. Carlson, New Palestine, IN (US)

( * ) Notice: Subject to any disclaimer, the term of this patent is extended or adjusted under 35 U.S.C. 154(b) by 1752 days.

(21) Appl. No.: 12/383,979

(22) Filed: Mar. 30, 2009

(65) Prior Publication Data

US 2009/0198131 A1     Aug. 6, 2009

Related U.S. Application Data

(63) Continuation of application No. 11/177,827, filed on Jul. 8, 2005, now abandoned.

(51) Int. Cl.
*A61N 7/02* (2006.01)
*A61B 19/00* (2006.01)

(52) U.S. Cl.
CPC ........... *A61N 7/02* (2013.01); *A61B 2019/5276* (2013.01)

(58) Field of Classification Search
CPC .............................................. A61B 2019/5276
USPC ........................................... 128/898; 606/27
See application file for complete search history.

(56) References Cited

U.S. PATENT DOCUMENTS

| 5,235,981 A | 8/1993 | Hascoet |
| 5,720,286 A | 2/1998 | Chapelon |
| 5,762,066 A | 6/1998 | Law et al. |
| 6,334,846 B1 * | 1/2002 | Ishibashi et al. .............. 600/439 |
| 6,533,726 B1 | 3/2003 | Lizzi et al. |
| 6,626,855 B1 | 9/2003 | Weng et al. |

FOREIGN PATENT DOCUMENTS

| EP | 0 685 211 | 12/1995 |
| EP | 06 78 6662 | 10/2009 |
| WO | WO 91/14400 | 10/1991 |

* cited by examiner

*Primary Examiner* — Aaron Roane
(74) *Attorney, Agent, or Firm* — Reed Smith LLP; Mark T. Vogelbacker

(57) ABSTRACT

A method and apparatus is disclosed for determining the success of a proposed HIFU Treatment, of an ongoing HIFU Treatment, and/or of a completed HIFU Treatment. An energy density of a given HIFU Treatment may be used as a comparison factor between the given HIFU Treatment and other HIFU Treatments and as a predictor of the success of the given HIFU Treatment. One exemplary energy density is the amount of energy deposited in the treatment region divided by the volume of the treatment region. Another exemplary energy density is the amount of energy deposited in the treatment region divided by the pre-treatment mass of the treatment region. A method and apparatus is disclosed to detect the presence of focal hyperechoic features and non-focal hyperechoic features. A method and apparatus is disclosed to detect the presence of an acoustic obstruction.

18 Claims, 20 Drawing Sheets

METHOD AND APPARATUS FOR THE TREATMENT OF TISSUE

RELATED APPLICATIONS

This application is a continuation application of U.S. application Ser. No. 11/177,827 filed on Jul. 8, 2005, now abandoned, which is herein incorporated by reference.

FIELD OF THE INVENTION

The present invention relates to an apparatus and related method for the treatment of tissue, and in particular, for the non-invasive treatment of diseased tissue.

BACKGROUND AND SUMMARY OF THE INVENTION

Several techniques have been used in the past for the treatment of tissue including diseased tissue, such as cancer, to remove, destroy, or otherwise minimize the growth of the diseased tissue. For example, traditional methods of treating diseased prostate tissue include high intensity focused ultrasound ("HIFU"), radiation, surgery, Brachytherapy, cryoablation, hormonal therapy, and chemotherapy. Described herein are improved apparatus and method for treating tissue with high intensity focused ultrasound.

Although the techniques, methods, and apparatus discussed herein have applicability to the treatment of tissue in general, this discussion will focus primarily on the treatment of prostate tissue including Benign Prostatic Hyperplasia (BPH) and prostatic cancer. However, the disclosed apparatus and methods will find applications in localization and treatment of a wide range of diseases which manifest themselves in a localized or "focal" manner, including cancers of the breast, brain, liver, and kidney. As explained herein, the disclosed apparatus uses an intracavity probe which will be particularly useful for focal diseases which are accessible to a transesophageal, laparoscopic or transvaginal probe. Such diseases include esophageal cancer, cancer in the trachea and urethra, ulcers in the stomach and duodenum, and pancreatic cancer. Moreover, a transvaginal probe according to the present invention will provide a minimally invasive sterilization procedure on an outpatient basis, as well as therapy for fibroids, and endometrial ablation. Additionally, in the case of a transducer with multiple focal lengths, blood vessels may be selectively targeted to effect coagulation and cauterization of internal bleeding.

As used herein the term "HIFU Therapy" is defined as the provision of high intensity focused ultrasound to a portion of tissue at or proximate to a focus of a transducer. It should be understood that the transducer may have multiple foci and that HIFU Therapy is not limited to a single focus transducer, a single transducer type, or a single ultrasound frequency. As used herein the term "HIFU Treatment" is defined as the collection of one or more HIFU Therapies. A HIFU Treatment may be all of the HIFU Therapies administered or to be administered, or it may be a subset of the HIFU Therapies administered or to be administered. As used herein the term "HIFU System" is defined as a system that is at least capable of providing a HIFU Therapy.

Various methods have been used to determine whether the above mentioned treatments are successful. The gold standard test is a biopsy of the tissue. However, other post treatment tests have been used in an attempt to determine the success of the above treatments. In the case of treating prostate tissue for prostate cancer, one such test is the level of prostate-specific antigen (PSA) in the blood at various times subsequent to testing. PSA is a serine protease normally produced in the prostate. However, both of these methods, biopsy and PSA monitoring, are conducted after the HIFU Treatment has been completed, typically many months later, and thus are not helpful in assisting the physician in determining either prior to the HIFU Treatment or during the HIFU Treatment the potential success of the HIFU Treatment.

Further, it is known to treat the whole prostate and to monitor the temperature of the prostate during treatment to determine if the temperature rise is sufficient to cause cell death. One method to monitor the temperature rise is to position a thermocouple in the prostate, but this is an invasive procedure. Another method to monitor temperature rise is to perform the HIFU Treatment while the patient is positioned within an MRI device. The MRI device is used to monitor the temperature rise in the prostate.

A need exists for a more reliable method of determining the success of a HIFU Treatment of a given treatment region. Additionally, a need exists for determining the success of a HIFU Treatment which does not subject the patient to invasive testing methods including biopsy and blood draws. Further, a need exists for a cost-effective, reliable method of determining the success of a HIFU Treatment after the completion of a HIFU Treatment, during a HIFU Treatment and/or prior to the commencement of a HIFU Treatment.

It is known that during the treatment of the prostate air bubbles between the probe and the rectal wall, such as between an acoustic membrane of the probe and the rectal wall, or calcification in the rectal wall may block the propagation of HIFU energy from being adequately delivered to the treatment site. Further, the application of HIFU energy in the presence of such an acoustic obstruction may result in damage to the rectal wall, such as a recto-urethral fistula. Traditionally, the physician is trained to observe multiple reverberations from an ultrasound image as an indication of an acoustic obstruction. A need exists for an automated method of detecting acoustic obstructions proximate to the rectal wall to avoid unwanted damage to the rectal wall.

In an exemplary embodiment of the present invention, a method of providing treatment to a treatment region of tissue is provided. The method comprising the steps of: planning a proposed HIFU Treatment of the treatment region; and determining prior to commencement of the proposed HIFU Treatment whether the proposed HIFU Treatment should be successful in treating the tissue of the treatment region. In an example, the determination of whether the proposed HIFU Treatment should be successful is based at least on an energy density of the energy planned to be deposited into the treatment region. In another example, the step of determining prior to commencement of the proposed HIFU Treatment whether the proposed HIFU Treatment should be successful in treating the tissue of the treatment region, comprises the steps of: calculating an energy density for the proposed HIFU Treatment; comparing the calculated energy density to a reference energy density; indicating that the proposed HIFU Treatment should be successful if the calculated energy density is greater than or equal to the reference energy density; and presenting the proposed HIFU Treatment to a reviewer for review if it is indicated that the proposed HIFU Treatment should be successful. In a further example, the step of planning the proposed HIFU Treatment of the treatment region comprises the steps of: generating a representation of the tissue; indicating a location of the treatment region on the representation of the tissue; and providing a plurality of proposed treatment sites within the treatment region, each of the proposed treatment sites having a proposed amount of energy to be deposited thereto. In one exemplary variation, the step of determining prior to commencement of the proposed HIFU Treatment whether the proposed HIFU Treatment should be successful in treating the tissue of the treatment region, comprises the steps of: calculating an energy density for the proposed HIFU Treatment; comparing the calculated energy density to a reference energy density; indicating that the proposed HIFU Treatment should be successful if the calculated energy density is greater than or equal to the reference energy density; and presenting the proposed HIFU Treatment to a reviewer for review if it is indicated that the proposed HIFU Treatment should be successful.

In another exemplary embodiment of the present invention, a method of determining the success of a given HIFU Treatment of a given treatment region is provided. The method comprising the steps of: providing a HIFU System to administer the given HIFU Treatment, the HIFU System including a transducer configured to provide a HIFU Therapy to a plurality of treatment sites and a controller configured to control the position and operation of the transducer; calculating an energy density for the given HIFU Treatment; comparing the calculated energy density to a reference energy density; and classifying the given HIFU Treatment as a successful HIFU Treatment based on the calculated energy density being greater than or equal to the reference energy density. In an example, the treatment region includes at least two treatment sub-portions, each treatment sub-portion including a subset of the plurality of treatment sites. In another example, the HIFU Treatment is a proposed HIFU Treatment and the step of calculating the energy density for the proposed HIFU Treatment includes the steps of: estimating an amount of energy to be deposited at each of the plurality of treatment sites; summing the amount of energy to be deposited at each of the plurality of treatment sites; and dividing the summed amount of energy to be deposited by one of a volume of the treatment region and a mass of the treatment region. In an exemplary variation, the method further comprises the steps of: preventing the HIFU Treatment from commencing if the calculated energy density is less than the reference energy density; and providing an override option whereby the reviewer may request that the HIFU Treatment commence even though the calculated energy density is less than the reference energy density. In a further example, the HIFU Treatment is a current HIFU Treatment and the step of calculating the energy density for the current HIFU Treatment includes the steps of: estimating an amount of energy deposited at each of the plurality of treatment sites which have received HIFU Therapy; estimating an amount of energy to be deposited at each of the plurality of treatment sites which have yet to receive HIFU Therapy; summing the amount of energy deposited at each of the plurality of treatment sites which have received HIFU Therapy and the amount of energy to be deposited at each of the plurality of treatment sites which have yet to receive HIFU Therapy; and dividing the summed amount of energy by one of a volume of the treatment region and a mass of the treatment region. In an exemplary variation, the method further comprises the step of: preventing the HIFU Treatment from progressing if the calculated energy density is less than the reference energy density; and providing an override option whereby the reviewer may request that the HIFU Treatment progress even though the calculated energy density is less than the reference energy density. In still a further example, the HIFU Treatment is a completed HIFU Treatment and the step of calculating the energy density for the completed HIFU Treatment includes the steps of: estimating an amount of energy deposited at each of the plurality of treatment sites; summing the amount of energy deposited at each of the plurality of treatment sites; and dividing the summed amount of energy deposited by one of a volume of the treatment region and a mass of the treatment region.

In a further exemplary embodiment of the present invention, an apparatus for treating tissue is provided. The apparatus comprising: a transducer which is positionable proximate to the tissue, the transducer being configured to emit ultrasound energy and to sense ultrasound energy; a positioning member coupled to the transducer and configured to position the transducer; and a controller operably coupled to the transducer and to the positioning member. The controller being configured to position the transducer with the positioning member and to operate the transducer in an imaging mode wherein images of the tissue are obtained from ultrasound energy sensed by the transducer and in a therapy mode wherein a plurality of treatment sites are treated with a HIFU Therapy with the transducer. The controller being further configured to plan a HIFU Treatment of a treatment region of the tissue to determine prior to commencement of the HIFU Treatment whether the HIFU Treatment should be successful in treating the tissue of the treatment region based on an energy density of the energy planned to be deposited into the treatment region. In an example, the controller is further configured to monitor the HIFU Treatment as the HIFU Treatment progresses to determine whether the HIFU Treatment should be successful in treating the tissue of the treatment region based on an amount of energy deposited into the treatment region and an amount of energy planned to be deposited in the treatment region. In another example, the apparatus further comprises a display operably coupled to the controller, the controller being configured to present the images of the tissue on the display and to provide a visual cue on the display of whether the planned HIFU Treatment should be successful in treating the tissue based on the amount of energy planned to be deposited into the treatment region and the amount of energy deposited in the treatment region. In a further example, the HIFU Treatment should be successful if the energy density is at least equal to a reference energy density.

In yet a further exemplary embodiment of the present invention, a computer-readable medium is provided. The computer readable medium providing instructions for directing a processor to: receive image information from a transducer; generate at least one image from the received image information; determine a treatment region based on the received image information; plan a HIFU Treatment of at least a portion of the treatment region, the HIFU Treatment including a plurality of treatment sites; calculate an energy density corresponding to the planned HIFU Treatment; provide an indication of whether the planned HIFU Treatment is likely to be successful based on the energy density; and control the transducer to conduct the planned HIFU Treatment. In an example, the instructions further direct the processor to prevent the planned HIFU Treatment from commencing if the planned HIFU Treatment is not likely to be successful based on the energy density. In another example, the instructions further direct the processor to monitor the planned HIFU Treatment as the planned HIFU Treatment progresses and to permit a modification to the planned HIFU Treatment. In an exemplary variation, the instructions further direct the processor to calculate an updated energy density corresponding to the planned HIFU Treatment with the modification and to provide an updated indication of whether the planned HIFU Treatment with the modification is likely to be successful based on the updated energy density. In another exemplary variation, the instructions further direct the processor to prevent a further progression of the planned HIFU Treatment with the modification if the updated energy density does not indicate that the planned HIFU Treatment with the modifications is likely to be successful. In a further example, the planned HIFU Treatment is likely to be successful if the energy density is at least equal to a reference energy density. In still a further example, the energy density is calculated by the steps of: estimating an amount of energy to be deposited at each of the plurality of treatment sites; summing the amount of energy to be deposited at each of the plurality of treatment sites; and dividing the summed amount of energy to be deposited by one of a volume of the treatment region and a mass of the treatment region.

In still a further exemplary embodiment of the present invention, a method of providing treatment to a treatment region of tissue with a HIFU Treatment, the HIFU Treatment including the provision of HIFU Therapy at spaced apart intervals to a plurality of treatment sites within the treatment region, is provided. The method comprising the steps of: driving the HIFU Treatment to generate a focal hyperechoic feature for a given treatment site; and maintaining the HIFU Treatment at a level to maintain the generation of subsequent focal hyperechoic features at subsequent treatment sites. In one example, the method further comprises the step of pausing the HIFU Treatment if a non-focal hyperechoic feature is generated. In an exemplary variation, the method further comprises the step of reducing the total acoustic power for subsequent treatment sites of the HIFU Treatment if a non-focal hyperechoic feature is generated which migrates from the respective focal zone.

In yet another exemplary embodiment of the present invention, a method of providing treatment to a treatment region of tissue with a HIFU Treatment, the HIFU Treatment including the provision of HIFU Therapy at spaced apart intervals to a plurality of treatment sites within the treatment region, is provided. The method comprising the steps of: distinguishing between a focal hyperechoic feature and a non-focal hyperechoic feature; continuing the HIFU Treatment upon the observance of the focal hyperechoic feature; and pausing the HIFU Treatment upon the observance of the non-focal hyperechoic feature. In an example, the step of distinguishing between a focal hyperechoic feature and a non-focal hyperechoic feature includes the steps of: generating a post-treatment image of a first treatment site; comparing a region of interest of the treatment region in the post-treatment image to the region of interest of the treatment region in a pre-treatment image; classifying the region of interest as containing a hyperechoic feature based on the comparison of the region of interest of the treatment region in the post-treatment image and the pre-treatment image; and comparing a location of the region of interest to a location of the treatment site, wherein the hyperechoic feature is classified as a focal hyperechoic feature if the location of the region of interest generally coincides with the location of the treatment site.

In still another exemplary embodiment of the present invention, an apparatus for treating tissue is provided. The apparatus comprising: a probe including an acoustic membrane covering at least a portion of the probe and a transducer positioned behind the acoustic membrane, the transducer being configured to emit ultrasound energy and to sense ultrasound energy; and a controller operably coupled to the transducer, the controller being configured to operate the transducer in an imaging mode wherein at least one image of the tissue is obtained from ultrasound energy sensed by the transducer and in a therapy mode wherein a plurality of treatment sites are treated with a HIFU Therapy with the transducer. The controller being further configured to detect the presence of an acoustic obstruction adjacent the acoustic membrane by detecting a repetitive pattern based on the at least one image of the tissue. In an example, the controller is further configured to prevent operation of the transducer in therapy mode based on a detection of an acoustic obstruction.

In a yet still a further exemplary embodiment of the present invention, a method of treating tissue in a treatment region is provided. The method comprising the steps of: imaging the treatment region with an ultrasound transducer; automatically detecting an acoustic obstruction proximate to the ultrasound transducer; and preventing the commencement of a HIFU Treatment based upon the detection of the acoustic obstruction proximate to the ultrasound transducer. In an example, the step of detecting the acoustic obstruction comprises the steps of: analyzing a portion of an image for a repetitive pattern, and determining the presence of the acoustic obstruction based on the presence of the repetitive pattern in the portion of the image. In an exemplary variation, the transducer is positioned within a probe behind an acoustic membrane of the probe and wherein the step of analyzing a portion of the image for a repetitive pattern comprises the steps of: analyzing a first portion of the image at about a position corresponding to the acoustic membrane and the tissue to determine if a first intensity characteristic associated with the first portion meets or exceeds a first upper threshold; analyzing a second portion of the image at about 1.5 times the position corresponding to the acoustic membrane and the tissue to determine if a second intensity characteristic associated with the second portion is below a first lower threshold; and analyzing a third portion of the image at about twice the position corresponding to the acoustic membrane and the tissue to determine if a third intensity characteristic associated with the third portion meets or exceeds a second upper threshold.

In yet still another exemplary embodiment of the present invention, a method of treating tissue in a treatment region with a HIFU Treatment is provided. The method comprising the steps of: initiating a HIFU Therapy to treat a portion of the tissue with an ultrasound transducer; obtaining an image of the treatment region subsequent to attempting to treat the portion of the tissue with HIFU Therapy; automatically detecting an acoustic obstruction proximate to the ultrasound transducer; and pausing the HIFU Treatment. In an example, the step of detecting the acoustic obstruction comprises the steps of: analyzing a portion of an image for a repetitive pattern, and determining the presence of the acoustic obstruction based on the presence of the repetitive pattern in the portion of the image. In an exemplary variation, the transducer is positioned within a probe behind an acoustic membrane of the probe and wherein the step of analyzing a portion of the image for a repetitive pattern comprises the steps of: analyzing a first portion of the image at about a position corresponding to the acoustic membrane and the tissue to determine if a first intensity characteristic associated with the first portion meets or exceeds a first upper threshold; analyzing a second portion of the image at about 1.5 times the position corresponding to the acoustic membrane and the tissue to determine if a second intensity characteristic associated with the second portion is below a first lower threshold; and analyzing a third portion of the image at about twice the position corresponding to the acoustic membrane and the tissue to determine if a third intensity characteristic associated with the third portion meets or exceeds a second upper threshold.

Additional features of the present invention will become apparent to those skilled in the art upon consideration of the following detailed description of the illustrative embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
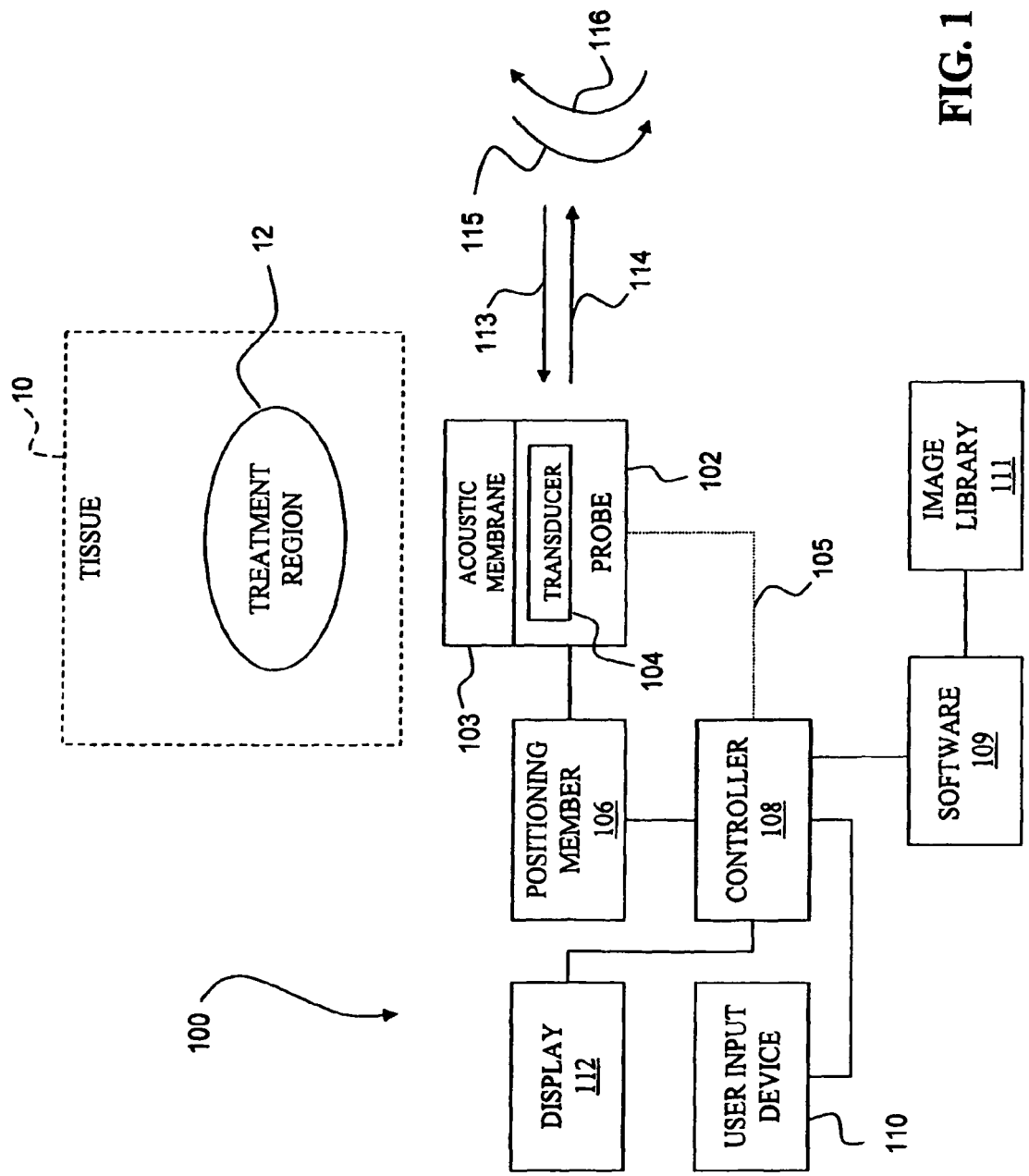
FIG. 1 is schematic view of an exemplary HIFU System of the present invention, the HIFU System being capable of imaging the tissue of the patient and to provide HIFU Therapy to at least a portion of the tissue at or proximate to a focus of a transducer of the HIFU System.

An exemplary HIFU System 100 is shown in FIG. 1. HIFU System 100 includes a probe 102 having a transducer member 104, a positioning member 106, a controller 108 operably coupled to probe 102 and the positioning member 106, a user input device 110 (such as keyboard, trackball, mouse, and/or touch screen), and a display 112. Probe 102 is operably connected to controller 108 through positioning member 106. However, as indicated by line 105 probe 102 may be directly connected with controller 108. Positioning member 106 is configured to linearly position transducer member 104 along directions 113, 114 and to angularly position transducer member 104 in directions 115, 116.

Transducer member 104 is positioned generally proximate to a region of tissue 10. In the case of the prostate, transducer 104 is positioned generally proximate to the prostate by the transrectal insertion of probe 102. Transducer member 104 is moved by positioning member 106 and controlled by controller 108 to provide imaging of at least a portion of tissue 10 including at least one treatment region 12 and to provide HIFU Therapy to portions of the tissue within at least one treatment region 12. As such, HIFU System 100 may operate in an imaging mode wherein at least a portion of tissue 10 may be imaged and in a therapy mode wherein HIFU Therapy is provided to portions of tissue 10 within at least one treatment region. As stated herein, treatment region 12 is defined as one or more portions of tissue which are to be treated during a HIFU Treatment. Treatment region 12 is illustratively shown as a continuous region. However, a treatment region might involve two or more distinct regions. In one example, illustrated in FIGS. 3C and 3D, treatment region 12 includes a plurality of treatment sub-portions, illustratively treatment segments 340a-f.

In one embodiment, transducer member 104 is a single crystal two element transducer. An exemplary transducer is disclosed in U.S. Pat. No. 5,117,832, the disclosure of which is expressly incorporated herein by reference. In a preferred embodiment, transducer 104 is capable of providing imaging of at least a portion of tissue 10 and of providing HIFU Therapy to at least a portion of tissue 10 within treatment region 12.

However, the present invention is not limited to the type of transducer implemented. On the contrary, various transducer geometries having a single focus or multiple foci and associated controls may be used including transducers which are phased arrays, such as the transducers disclosed in pending U.S. patent application Ser. No. 11/070,371, filed Mar. 2, 2005, titled "Ultrasound Phased Arrays," the disclosure of which is expressly incorporated herein by reference. Additional exemplary transducers and associated controls are disclosed in U.S. Pat. No. 5,762,066; U.S. Abandoned patent application Ser. No. 07/840,502 filed Feb. 21, 1992; Australian Patent No. 5,732,801; Canadian Patent No. 1,332,441; Canadian Patent No. 2,250,081; U.S. Pat. Nos. 5,036,855; 5,492,126; 6,685,640, each of which is expressly incorporated herein by reference.

Figure 15A:
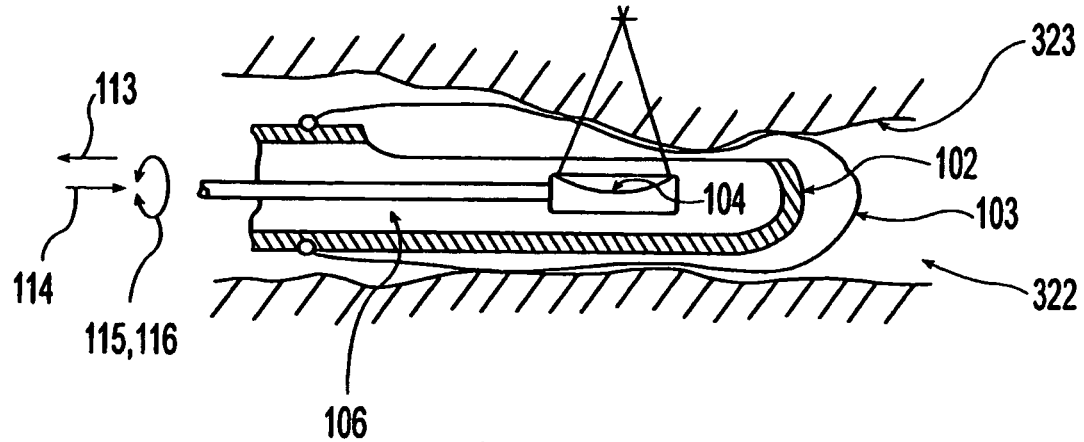
FIG. 15A is a representation of the rectum of the patient along with the probe, the transducer, and an acoustic membrane covering a portion of the probe of the HIFU System of FIG. 1.
Figure 15B:
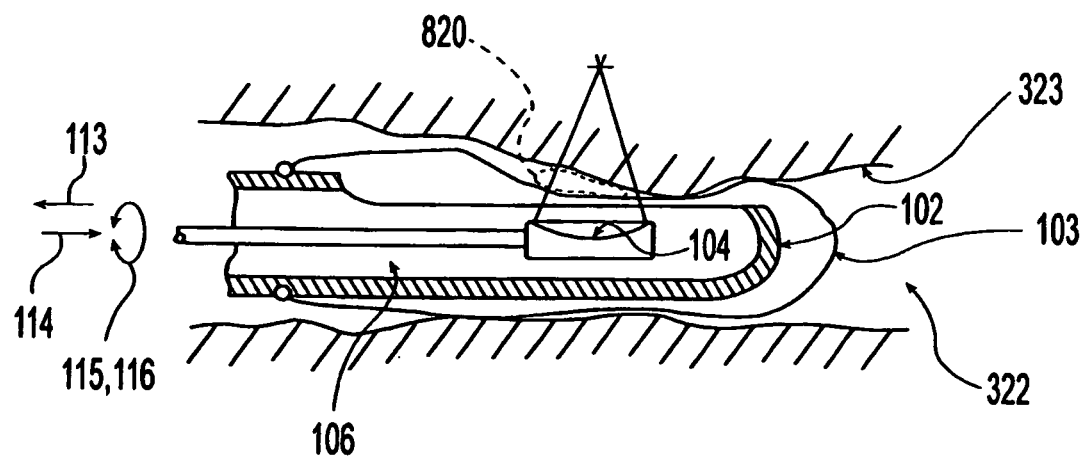
FIG. 15B is a representation of the view of FIG. 15A wherein an acoustic obstruction is positioned proximate to the transducer, illustratively between the acoustic membrane and the rectal wall.

In one embodiment, a portion of probe 102 is covered by an acoustic membrane 103. Acoustic membrane 103 is an expandable membrane whose overall size is increased by placing a fluid on an interior of acoustic membrane 103. In one embodiment, the fluid is water or a generally acoustic transparent material and is provided by a reservoir or a chiller. The fluid may be used to remove heat from proximate to transducer 104 as well as expanding acoustic membrane 103. In one embodiment, acoustic membrane 103 is expanded such that it contacts or generally is adjacent to the surrounding tissue, such as rectal wall 323, as shown in FIG. 15A. In one embodiment, acoustic membrane 103 is a condom placed over a tip of probe 102, sealed with o-rings, and filled with water. Exemplary acoustic membranes and details of their operation in relation to respective other portions of exemplary HIFU Systems are provided in U.S. Pat. Nos. 5,762,066, 5,993,389, and U.S. Provisional Patent Application Ser. No. 60/686,499, filed Jun. 1, 2005, the disclosures each of which are expressly incorporated by reference herein.

In one embodiment, controller 108 is configured to execute one or more of the methods discussed herein. In one embodiment, at least a portion of each method executed by controller 108 is provided as a portion of software 109.

Figure 2:
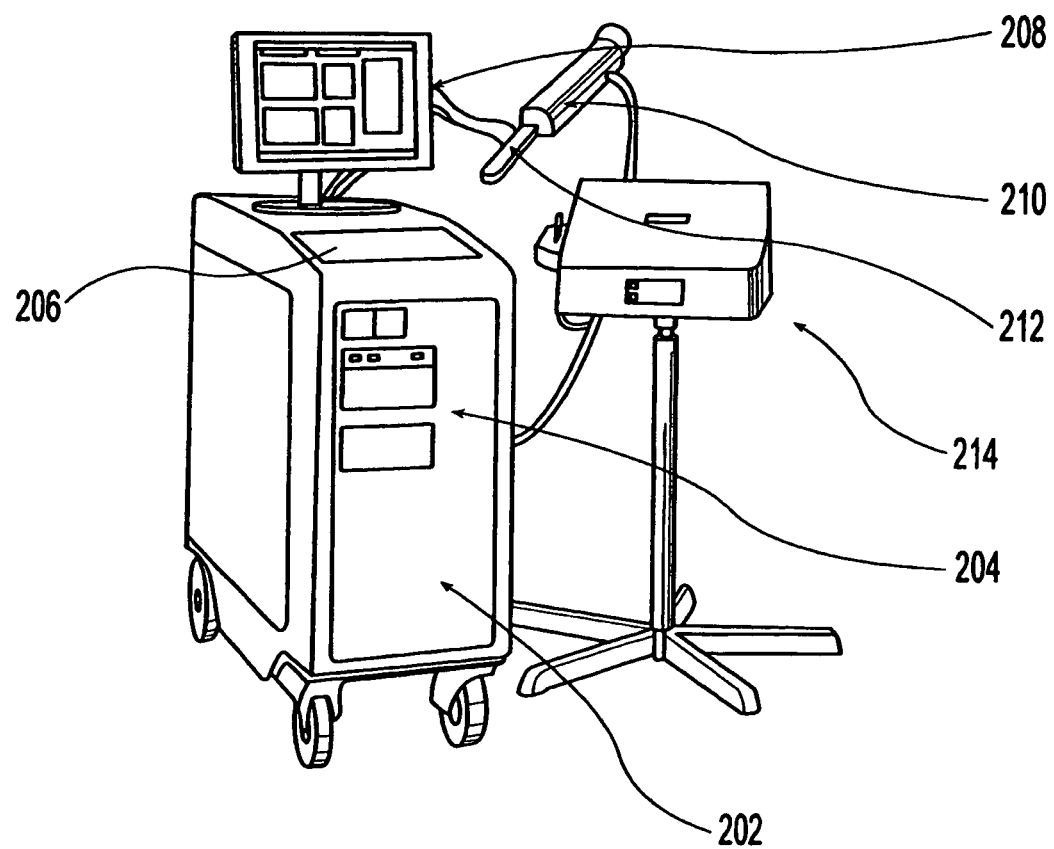
FIG. 2 is an exemplary embodiment of the HIFU System of FIG. 1.

Referring to FIG. 2, an exemplary HIFU System 200 is shown, the Sonablate® 500 HIFU System available from Focus Surgery, Inc., located at 3940 Pendleton Way, Indianapolis, Ind. 46226. HIFU System 200 includes a console 202 which houses or supports a controller (not shown), such as a processor and associated software; a printer 204 which provides hard copy images of tissue 10 and/or reports (see FIG. 8B); a user input device 206 such as a keyboard, trackball, and/or mouse; and a display 208 for displaying images of tissue 10 and software options to a user, such as a color display. Further, shown is a probe 210 which includes a transducer member (not shown), and a positioning member (not shown). Also shown is an articulated probe arm 212 which is coupled to console 202. Articulated probe arm 212 orients and supports probe 210. A chiller 214 is also shown. Chiller 214, in one embodiment, provides a water bath with a heat exchanger for the transducer member of probe 210 to actively remove heat from the transducer member during a HIFU Treatment.

Further details of suitable HIFU Systems which may be modified to execute the methods described herein are disclosed in U.S. Pat. Nos. 4,084,582; 4,207,901; 4,223,560; 4,227,417; 4,248,090; 4,257,271; 4,317,370; 4,325,381; 4,586,512; 4,620,546; 4,658,828; 4,664,121; 4,858,613; 4,951,653; 4,955,365; 5,036,855; 5,054,470; 5,080,102; 5,117,832; 5,149,319; 5,215,680; 5,219,401; 5,247,935; 5,295,484; 5,316,000; 5,391,197; 5,409,006; 5,443,069; 5,470,350, 5,492,126; 5,573,497; 5,601,526; 5,620,479; 5,630,837; 5,643,179; 5,676,692; 5,840,031; 5,762,066; 6,685,640; U.S. Abandoned patent application Ser. No. 07/840,502 filed Feb. 21, 1992; Australian Patent No. 5,732, 801; Canadian Patent No. 1,332,441; Canadian Patent No. 2,250,081; U.S. patent application Ser. No. 11/070,371, filed Mar. 2, 2005, titled "Ultrasound Phased Arrays;" U.S. Provisional Patent Application No. 60/568,556, filed May 6, 2004, titled "Treatment of Spatially Oriented Disease with a Single Therapy, Imaging, and Doppler Ultrasound Transducer;" PCT Patent Application Serial No. US2005/015648, filed May 5, 2005, designating the US, titled "Method and Apparatus for the Selective Treatment of Tissue", the disclosures each of which is expressly incorporated herein by reference.

As explained herein, HIFU System 100 is configured to provide a predictor of the success of a given HIFU Treatment during the planning portion of the given HIFU Treatment, during the performance of the HIFU Treatment, and/or subsequent to the completion of the HIFU Treatment. In one exemplary embodiment, controller 108 includes software 109 which when executed determines whether the given HIFU Treatment was likely successful or will likely result in a successful treatment. Further, software 109 controls the operation of HIFU System 100 including the imaging, planning, and treatment operations.

Figure 3A:
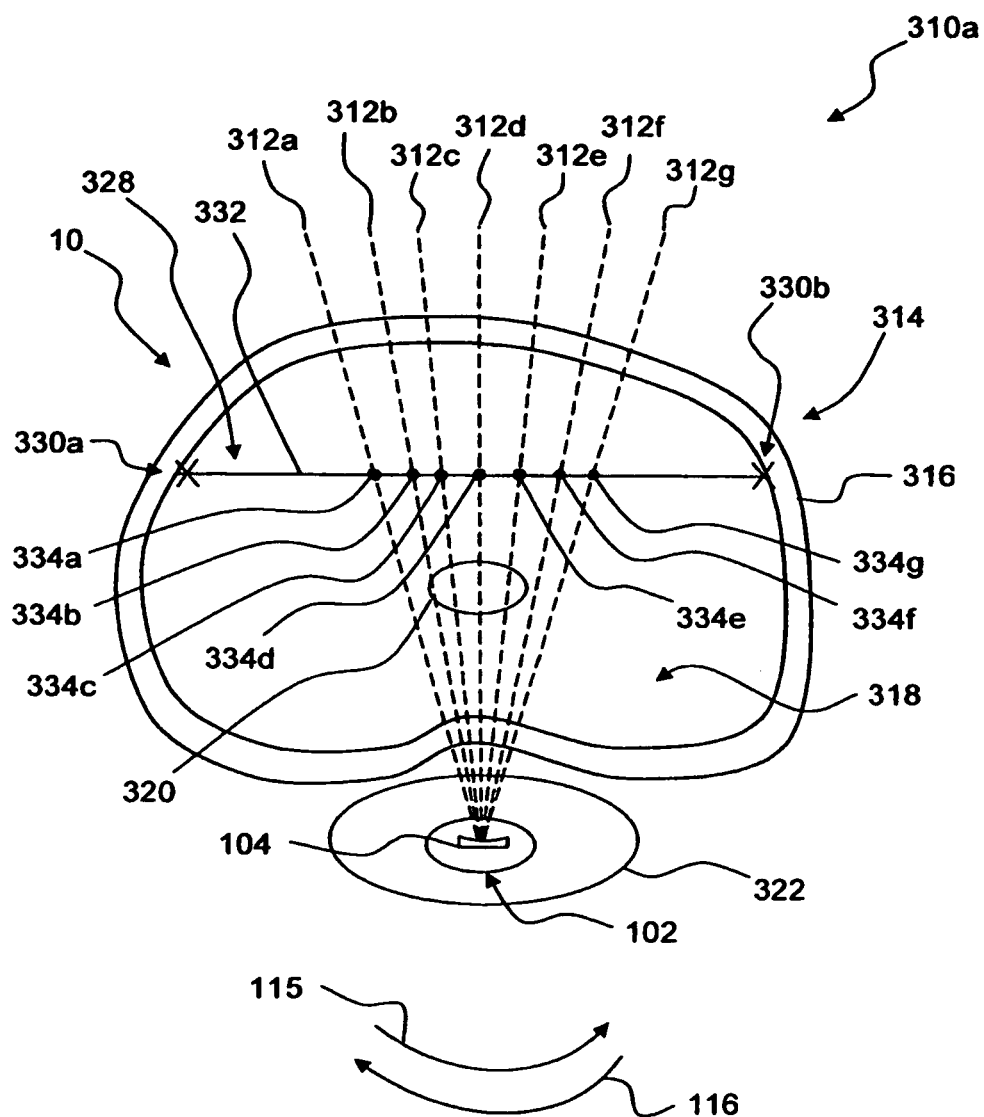
FIG. 3A is a representation of a transverse or sector view of the prostate and rectum of the patient along with the probe and the transducer of the HIFU System of FIG. 1.
Figure 3B:
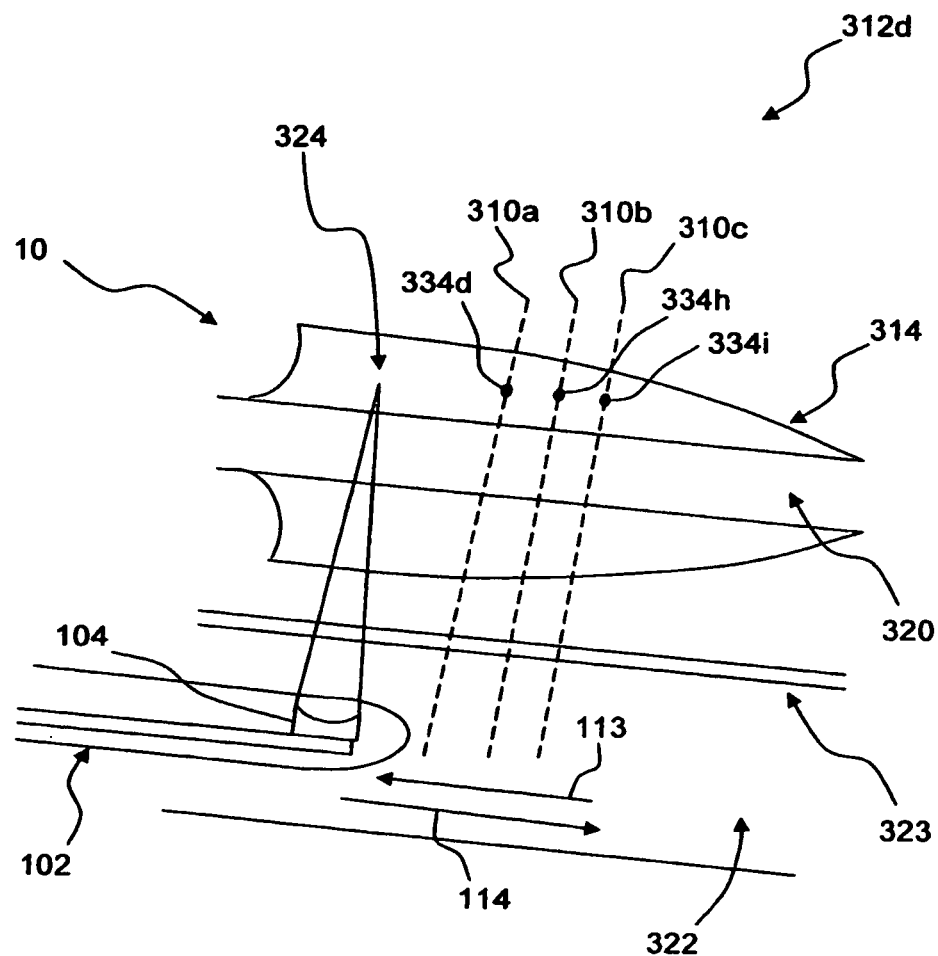
FIG. 3B is a representation of a longitudinal or linear view of the prostate and rectum of the patient along with the probe and the transducer of the HIFU System of FIG. 1.
Figure 3C:
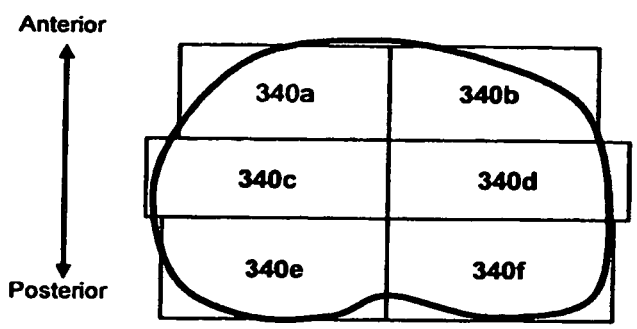
FIG. 3C is a representation of a transverse or sector view of the prostate of the patient wherein the whole prostate corresponds to the treatment region, the treatment region illustratively including six treatment segments.
Figure 3D:
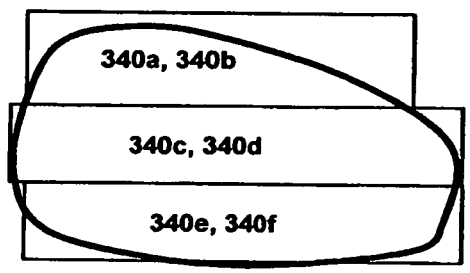
FIG. 3D is a representation of a longitudinal or linear view of the prostate of the patient wherein the whole prostate corresponds to the treatment region, the treatment region illustratively including six treatment segments.
Figure 4:
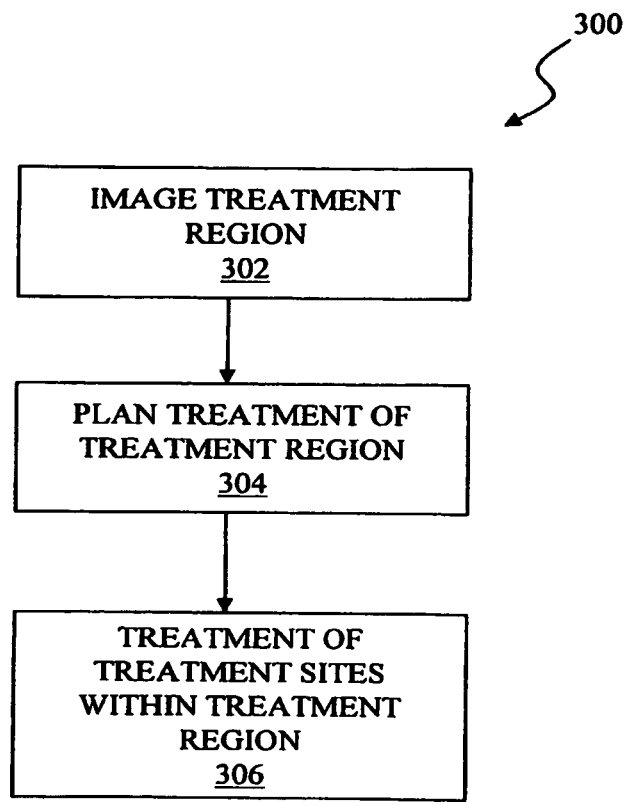
FIG. 4 is an exemplary process for an exemplary HIFU Treatment.

Referring to FIGS. 3A-3D and FIG. 4, an overview of an HIFU Treatment with HIFU System 100 is explained. Referring to FIG. 4, an exemplary HIFU Treatment 300 includes the imaging of the treatment region and/or surrounding tissue, as represented by block 302; the planning of a HIFU Treatment, as represented by block 304; and the performance of the HIFU Treatment, as represented by block 306.

In a first exemplary embodiment, the treatment region and surrounding tissue is imaged with HIFU System 100 using conventional ultrasound techniques. HIFU System 100 generates and stores a plurality of 2-D images of tissue 10 including treatment region 12. In one example, HIFU System 100 generates and stores a plurality of transverse or sector images about every 3 mm along the treatment region (as represented by lines 310a-c in FIG. 3B) and generates and stores a plurality of longitudinal or linear images about every 3° (as represented by lines 312a-g in FIG. 3A). In other examples, different spacing of the transverse and longitudinal images are used.

As used herein, the term "treatment region" is defined as one or more portions of tissue which are to be treated during a HIFU Treatment. In general, treatment region is used to describe the overall area being treated during a HIFU Treatment. However, treatment region may also be used to describe one or more sub-regions of the overall area being treated, such as one or more treatment segment(s) and/or one or more treatment site(s).

Referring to FIGS. 3A and 3B, in the application of treating prostate cancer, tissue 10 includes the prostate 314 of the patient, the prostate 314 having a capsule 316 and cancerous tissue 318 located within the interior of capsule 316. As is known, prostate 314 surrounds urethra 320 and is positioned proximate to the rectum 322 having a rectal wall 323. Rectum 322 receives probe 102 of HIFU System 100 such that transducer 104 is positioned proximate to prostate 314. Transducer 104 is used to image tissue 10 as represented by lines 310a-c in FIG. 3B (transverse images) and by lines 312a-g in FIG. 3A (longitudinal images). Further, transducer 104 is used to provide HIFU Therapy to tissue 10, illustratively to tissue 324 in FIG. 3B.

Based on the 2-D images generated and stored, the physician is able to plan the HIFU Treatment, as represented by block 304 in FIG. 4. In one embodiment, the physician examines an image on display 112 and with user input device 110 marks the boundaries of a treatment segment 328, as represented by endpoints 330a,b and line 332 in FIG. 3A. Based on treatment segment 328, HIFU System 100 generates a plurality of treatment sites or zones which generally correspond to the intersection of treatment segment 328 and imaged locations of tissue 10 (tissue which has at least one of or preferably both of a corresponding transverse image and a corresponding longitudinal image). An exemplary treatment site 334*d* is shown in FIGS. 3A and 3B and is imaged in both images 310*a* (generally corresponding to the plane of FIG. 3A) and image 312*d* (generally corresponding to the plan of FIG. 3B). Treatment segments 328 may be generated on either transverse images (310*a-c*) and/or longitudinal images (312*a-g*). In alternative embodiments, treatment sites do not correspond to imaged locations of tissue.

By restricting treatment sites 334 to imaged tissue locations, the physician is able to see images of the representative tissue prior to HIFU Therapy and immediately following HIFU Therapy or at further times subsequent to HIFU Therapy. Thus, the physician may compare the treated tissue to its pre-HIFU state. Also, the physician is able to monitor the treatment site and surrounding tissue for the hyperechoic features as described herein.

As stated herein, in one embodiment it is desirable to observe focal hyperechoic features at a treatment site subsequent to treatment with HIFU Therapy. Further, it is generally undesirable to observe non-focal hyperechoic features subsequent to treatment with HIFU Therapy. As used herein a focal hyperechoic feature is defined as a hyperechoic feature which is generally confined to a focal zone of a treatment site. As used herein a non-focal hyperechoic feature is defined as a hyperechoic feature which is generally treatment site specific and migrates from the focal zone of the treatment site, such as towards the transducer.

In one embodiment, a plurality of images, such as a plurality of transverse images are simultaneously displayed on display 112, such that the physician may plan treatment segments on multiple images while still viewing related images. In one embodiment, display 112 is capable of displaying the number of images which correspond to the complete linear movement of transducer 104. In one example, transducer 104 may be linearly moved a range of about 45 mm and tissue 10 is imaged at 3 mm intervals. Thus, fifteen transverse images are displayed on display 112 at the same time. In general, the fifteen transverse images spaced at about 3 mm provide images of the entire prostate.

Referring to FIGS. 3C and 3D, exemplary treatment segments 340*a-f* are shown. Treatment segments 340*a-f* cover the entire prostate 314. Each segment is defined as a region in the treatment zone including a plurality of treatment sites. In one embodiment, a HIFU Treatment consists of multiple treatment segments positioned such that the substantially whole prostate is within the treatment region.

During a HIFU Treatment, treatment segments 340*a-f* are treated in successive order. For a given treatment segment, transducer 104 is moved to coincide with the treatment segment and the focal length of the transducer is chosen. In one example, transducer 104 has two focal lengths, 30 mm and 40 mm. In one embodiment, treatment sites in a given treatment segment are treated with HIFU Therapy by rotating the transducer transverse to the probe axis and then treating all of the sites at that angular or sector position by systematically translating transducer 104 from one end of a given treatment segment to the other end of the treatment segment in one of directions 113, 114. This systematic treatment is then repeated for each angular or sector position within the treatment segment.

HIFU Therapy greatly changes the acoustic (physical) properties of tissue. Thus, in one embodiment the treatment segments farthest from the transducer (anterior side) are treated first with the treatment progressing towards the position of the probe (posterior side). There is very little change in the value of the TAP setting for the treatment sites within a given treatment segment. In one example, a HIFU Therapy is provided for 3 seconds at an excitation frequency of about 4 MHz plus/minus about 50 KHz. In addition, the focal distance is the same and the tissue path is similar for all treatment sites within a treatment segment. In one example, to limit the change in the physical properties of the tissue between the transducer member 104 of probe 210 and the treatment segment, sector positions as demonstrated in FIG. 3A by treatment sites 334*a-g* within a given treatment segment are not treated successively, but rather in a spaced manner. In the linear direction for a given treatment segment, the order of treatment sites is generally successive. Referring to FIG. 3B, treatment sites are generally treated in the following order 334*i*, 334*h*, and 334*d*. Referring to FIG. 3A, the order of the sector positions when treating a treatment segment is interleaved in the following order: 334*d*; 334*f*; 334*b*; 334*e*; 334*c*; 334*g*; and 334*a*. In another example, the sector position order may be alternating from inside of the treatment segment towards the outside of the treatment segment resulting in the following order: 334*d*; 334*e*; 334*c*; 334*f*; 334*b*; 334*g*; and 334*a*. In another example, the sector position order may be alternating from outside of the treatment segment towards the inside of the treatment segment resulting in the following order: 334*a*; 334*g*; 334*b*; 334*f*; 334*c*; 334*e*; and 334*d*. In another example, the sector positions are ordered successively from 334*a-g*.

In one embodiment, a three-dimensional model of tissue 10 is construed based on the plurality of 2-D images of tissue 10. In one example, the three-dimensional model is construed based on the 2-D images of tissue 10 and/or 3-D images of tissue 10 and Doppler imaging of tissue 10. Example tissue components modeled include one or more of prostate 314, prostate capsule 316, urethra 320, rectum 322, and rectal wall 323. An explanation of exemplary methods and apparatus to calculate a three-dimensional model of the prostate and/or other tissue components are disclosed in U.S. Provisional Patent Application No. 60/568,556, filed May 6, 2004, titled "Treatment of Spatially Oriented Disease with a Single Therapy, Imaging, and Doppler Ultrasound Transducer," and PCT Patent Application Serial No. US2005/015648, filed May 5, 2005, designating the US, titled "Method and Apparatus for the Selective Treatment of Tissue", the disclosures each of which is expressly incorporated herein by reference.

In one embodiment, HIFU System 100 generates a HIFU Treatment plan to treat substantially all of prostate 314, the HIFU Treatment plan being based in part on the three-dimensional model of prostate 314 and/or additional tissue components. Exemplary methods and apparatus to generate the HIFU Treatment plan are disclosed in U.S. Provisional Patent Application No. 60/568,556, filed May 6, 2004, titled "Treatment of Spatially Oriented Disease with a Single Therapy, Imaging, and Doppler Ultrasound Transducer," and PCT Patent Application Serial No. US2005/015648, filed May 5, 2005, designating the US, titled "Method and Apparatus for the Selective Treatment of Tissue", the disclosures each of which is expressly incorporated herein by reference.

In one exemplary embodiment, a method for predicting the success of a HIFU Treatment is based on the density of energy deposited ($E_{Deposition}$) to the tissue in the treatment region. In one example, the density of the energy deposition is obtained by dividing the total energy deposited within the tissue in the treatment region by the volume of the treatment region ($J/cm^3$). In another example, the density of the energy deposition is obtained by dividing the total energy deposited within the tissue in the treatment region by the pre-treatment mass of the tissue in the treatment region (J/g). By using a density value a first HIFU Treatment having a first treatment region size, such as for patient A, may be easily compared to a second HIFU Treatment having a different second treatment region size, such as for patient B. As such, an exemplary density of the energy deposition ($E_{Deposition}$) may be obtained by dividing the energy deposited to the tissue by the mass of the treatment region; expressed as:

$$E_{Deposition} = \frac{E}{M_{TreatmentRegion}} \quad (1)$$

wherein $E_{Deposition}$ is the density of the energy deposition, E is the energy deposited to the tissue in the treatment region and $M_{TreatmentRegion}$ is the mass of the treatment region.

In an illustrated example, the prostate is being treated with a HIFU Treatment. In the illustrated example, substantially the whole prostate is being treated. As such, the size of the treatment region is generally equal to the size of the prostate itself. The density of the energy deposition ($E_{Deposition}$) may be calculated by the following equation:

$$E_{Deposition} = \frac{\sum_{All\ Sites}(1-e^{-\alpha_{site}L_{site}})A_{site}TAP_{site}t_{ON}}{M_{prostate}} \quad (2)$$

wherein: $TAP_{site}$ is the total acoustic power applied at each treatment site or zone; $t_{ON}$ is the time duration that HIFU energy is being applied; $A_{site}$ is the attenuation arising from propagation through tissue before the HIFU Treatment site or zone; $\alpha_{site}$ is the intensity attenuation coefficient in Np/cm (Np=nepers) which accounts for the energy absorbed by the acoustic wave within the treatment zone; $L_{site}$ is the length of the treatment zone tissue path for each treatment site; and $M_{prostate}$ is the measurement of the prostate mass which is determined in part based on transrectal ultrasound imaging with the HIFU System as explained herein.

The parameters $L_{site}$, $t_{on}$, and $A_{site}$ may be either estimated or inferred based on the location of the treatment site and the parameters of the HIFU System. $A_{site}$ may be determined from the following equation:

$$A_{site} = \prod_{layer} e^{-\alpha_{layer}L_{layer}}, \quad (3)$$

wherein $\alpha_{layer}$ and $L_{layer}$ are the intensity attenuation coefficient and the layer length respectively. For the example of treating the prostate (assuming the whole prostate is the treatment region) $A_{site}$ may be estimated to be equal to one if the rectal wall (FIG. 3B) is ignored and the water before the prostate is approximated with an attenuation coefficient of zero. (As stated herein, transducer 104 is within a water bath supplied by chiller 214.) As such, the only parameters still requiring a method of measurement or estimation are the total acoustic power applied at each treatment site ($TAP_{site}$), the mass of the prostate ($M_{prostate}$), and the intensity attenuation coefficient at each site ($\alpha_{site}$).

The intensity at the focus ($I_{focus}$) of the transducer being used for treatment may be determined from the following equation:

$$I_{focus} = \frac{1}{f_{area}} TAP_{site} e^{-\alpha_{site}L_{site}} \quad (4)$$

wherein $f_{area}$ is the area of the focus of the transducer, $\alpha_{site}$ is the intensity attenuation coefficient in Np/cm which accounts for the energy absorbed by the acoustic wave within the treatment zone; and $L_{site}$ is the length of the treatment zone tissue path for each treatment site. As stated above $L_{site}$ may be estimated from the location of the treatment site and the parameters of the HIFU System. $f_{area}$ may be measured or estimated. $TAP_{site}$ may be measured for the transducer as a function of excitation energy with an acoustic power meter, such as the UPM-DT-10 Ultrasound Power Meter available from Ohmic. Instruments Company, located in Easton, Maryland.

The mass of the prostate ($M_{prostate}$) may be calculated by multiplying the volume of the prostate by about 1.050 gm/cm³. However, as stated herein the volume of the prostate may be used to determine the density of the energy deposition instead of the mass of the prostate. In one embodiment, the volume of the prostate is estimated using a prolate ellipsoid formula which is based on a normal untreated prostate shape and is expressed as $$V_{prostate} = 0.52 W_T H_{AtoP} L_L. \quad (5)$$

wherein $V_{prostate}$ is the volume of the prostate; $W_T$ is the transverse width; $H_{AtoP}$ is the anterior to posterior height of the prostate; $L_L$ is the longitudinal length of the prostate capsule. The three parameters $W_T$, $H_{AtoP}$, and $L_L$ are measurable from the two dimensional transrectal ultrasound images of the prostate. In one example, the physician marks the locations of the treatment region by marking on the two dimensional images the endpoints for the above three parameters. Software 109 of HIFU System 100 then calculates the values for each parameter and the value for $V_{prostate}$. In one embodiment, software 109 of HIFU System 100 automatically locates the endpoints of the above three parameters and calculates the $V_{prostate}$ for a given prostate. Similarly looking at images of a prostate, a user may readily indicate the endpoints for the above parameters and manually calculate the volume of the prostate.

In another embodiment, the volume of the prostate is estimated by calculating a three-dimensional model of the actual prostate from two dimensional transrectal ultrasound images. This method provides a more accurate volume of the prostate than the prolate ellipsoid formula. An explanation of exemplary methods and apparatus to calculate a three-dimensional model of the prostate and/or other tissue components are disclosed in U.S. Provisional Patent Application No. 60/568,556, filed May 6, 2004, titled "Treatment of Spatially Oriented Disease with a Single Therapy, Imaging, and Doppler Ultrasound Transducer," and PCT Patent-Application Serial No. US2005/015648, filed May 5, 2005, designating the US, titled "Method and Apparatus for the Selective Treatment of Tissue", the disclosures each of which is expressly incorporated herein by reference.

The tissue intensity attenuation coefficient, $\alpha_{site}$, varies as a function of frequency. For acoustic energy being delivered to the prostate at about 4.0 MHz $\alpha_{site}$ is about 0.64 Np/cm. Since all of the parameters of equation 2 may now be measured or estimated, the density of the energy deposition may be calculated for a completed HIFU Treatment of the prostate, a current HIFU Treatment of the prostate, and/or a planned HIFU Treatment of the prostate. Further, since the density of the energy deposition ($E_{Deposition}$) is a density value, it is possible to compare a first HIFU Treatment to a second HIFU Treatment regardless of the sizes of the respective treatment regions.

In order to evaluate the ability of the density of the energy deposition ($E_{Deposition}$) to function as a predictor of the success of a HIFU Treatment in the treatment of prostate cancer, data from a sample of twenty patients was analyzed. Each of the patients had participated in a clinical trial at the Indiana University School of Medicine in Indiana wherein each was treated for prostate cancer with the Sonablate® 500 HIFU System. A biopsy of the prostate was analyzed at 180 days after HIFU Treatment for nineteen of the participants (1 participant died prior to 180 days of an unrelated myocardial infarction). A positive biopsy was defined as a treatment failure and a negative biopsy was defined as a treatment success.

The density of the energy deposition ($E_{Deposition}$) was calculated for each participant using two different values for $\alpha_{site}$ ($\alpha_{site}=\infty$ and $\alpha_{site}=0.64$ Np/cm). Setting $\alpha_{site}$ to infinity is equivalent to stating that all of the HIFU energy is absorbed by the prostate. For each of the nineteen subjects and for both values of $\alpha_{site}$, the total acoustic power (TAP) values for three sites (first site, center site, last site) within a given treatment segment were averaged and used as the basis for the TAP value of all sites in the given treatment segment. $t_{ON}$ for each site was 3 seconds. As discussed above $A_{site}$ was set to one. The mass of the prostate $M_{prostate}$) for each subject was estimated using a prolate ellipsoid formula that is based on the normal/untreated prostate shape.

For the case of assuming that $\alpha_{site}$ is equal to infinity, equation 2 may be expressed as:

$$E_{Deposition} = \frac{\sum_{All\ Sites} TAP_{site} t_{ON}}{M_{prostate}}. \quad (6)$$

Figure 5:
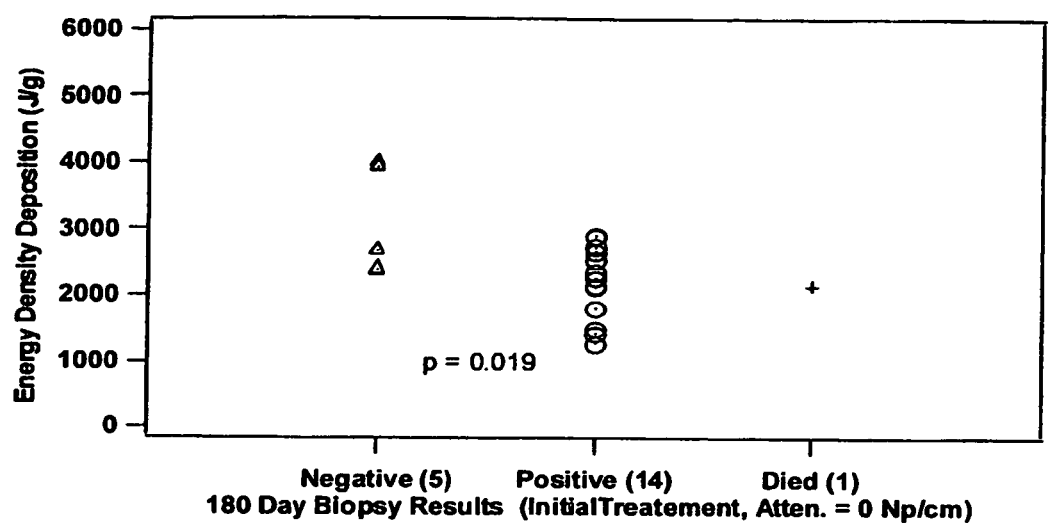
FIG. 5 is a Student's t-test of a calculated density of the energy deposition for a sample of patients which had biopsies subsequent to a HIFU Treatment, the density of the energy deposition being calculated with the assumption that the intensity attenuation coefficient is equal to infinity.

The density of the energy deposition ($E_{Deposition}$) for each patient was calculated. The density of the energy deposition ($E_{Deposition}$) for each patient is shown in FIG. 5. The density of the energy depositions are shown with the negative and positive biopsies in separate columns. Referring to FIG. 5, a discernable spread is shown between the density of the energy deposition ($E_{Deposition}$) for the patients that had a negative biopsy and for patients that had a positive biopsy. The value indicated as p in FIG. 5 represents the probability that the distribution of the density of the energy deposition results are the same for patients that had a negative biopsy and for patients that had a positive biopsy. If p is less than 0.05, the conclusion is that there is a significant difference between the density of energy deposition results for the two groups of patients. Thus the result shown in FIG. 5 demonstrates that there is a 98.1% probability that the density of energy deposition is different for the two groups of patients.

Figure 6:
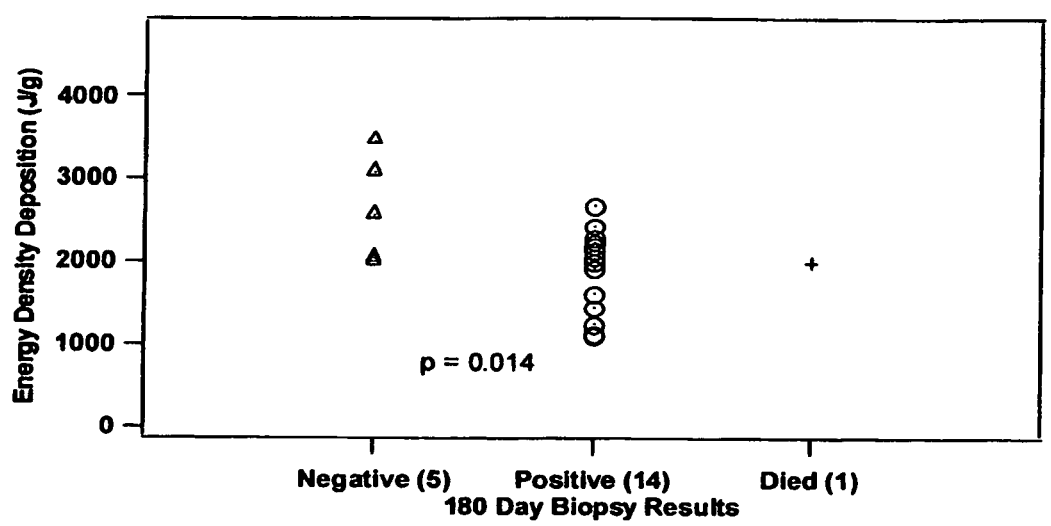
FIG. 6 is a Student's t-test of a calculated density of the energy deposition for a sample of patients which had biopsies subsequent to a HIFU Treatment, the density of the energy deposition being calculated with the assumption that the intensity attenuation coefficient is equal to 0.64 Np/cm.

For the case of assuming that $\alpha_{site}=0.64$ Np/cm, equation 2 is used to calculate the density of the energy deposition ($E_{Deposition}$) for each patient. The differences in the density of the energy deposition ($E_{Deposition}$) for each patient is shown in FIG. 6. The density of the energy depositions are shown with the negative and positive biopsies in separate columns. Referring to FIG. 6, a significant difference is demonstrated between the density of energy deposition ($E_{Deposition}$) for patients that had a negative biopsy and for patients that had a positive biopsy. For the data shown in FIG. 6, the probability that the density of energy deposition is different for the two groups of patients is 98.6%.

Both FIGS. 5 and 6 demonstrate that the density of the energy deposition ($E_{Deposition}$) appears to be a predictive factor in the ability to determine the success or failure of a given HIFU Treatment of the prostate. In order to determine the ability of the density of the energy deposition as a deciding factor in determining the success or failure of a given HIFU treatment, a receiver operator characteristic (ROC) analysis was applied for the nineteen patients discussed above and for each of the intensity attenuation coefficient values ($\alpha_{site}$). For both attenuation settings ($\alpha_{site}$), the 'gold standard' test for cancer was the post-treatment 180 day biopsy result, whereas the test being measured by the ROC analysis is the density of the energy deposition ($E_{Deposition}$) given by equation (2) or equation (6) in the case of $\alpha_{site}$ equal to infinity.

The first step in the ROC analysis is to obtain a data set that includes both the test (density of the energy deposition) and the corresponding 'gold standard' measure (biopsy of prostate). Then an array of decision levels are created that span the range of the test values (density of the energy deposition levels). A 2 by 2 table is created that follows the template shown in Table 1.

TABLE 1

| | Biopsy (Positive) | Biopsy (Negative) |
|---|---|---|
| $E_{Deposition}$ (Lower than Threshold) | True Positive (TP) | False Positive (FP) |
| $E_{Deposition}$ (Higher than Threshold) | False Negative (FN) | True Negative (TN) |

In the template shown in Table 1, the columns represent the 'gold standard' (Biopsy), while the rows represent the test ($E_{Deposition}$). From this table two key quantities may be defined:

$$\text{Sensitivity} = \frac{TP}{(TP+FN)} \quad (7)$$

$$\text{Specificity} = \frac{TN}{(FP+TN)} \quad (8)$$

The sensitivity is a measure of how well the test detects the parameter sought, in this case subjects which will have positive biopsies 180 days after treatment. The specificity is a measure of how well the test excludes those without the parameter sought, in this case subjects which will have negative biopsies 180 days after treatment.

Figure 7:
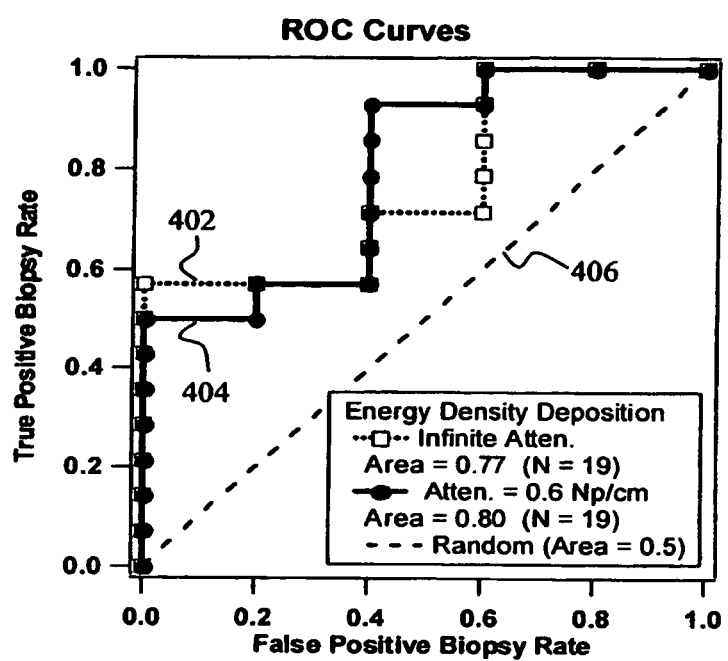
FIG. 7 is an exemplary receiver operator characteristic curve (ROC) for the density of the energy depositions and biopsy results shown in FIGS. 5 and 6, the ROC in this case provides a measure of the ability of a test to determine if the density of the energy deposition represents a diseased or not diseased state.

The next step in ROC analysis is to plot the sensitivity or true positive rate as a function of the false positive rate or (1-specificity). The area under the curve that is created provides a measure of the ability of the test to determine a case of disease (positive biopsy) from a case of no disease (negative biopsy). Referring to FIG. 7, the ROC curves for the two cases $\alpha_{site}=\infty$ and $\alpha_{site}=0.64$ Np/cm) are shown. Curve 402 corresponds to the case of $\alpha_{site}=\infty$. Curve 404 corresponds to the case of $\alpha_{site}=0.64$ Np/cm. Each curve was constructed from data points, each of which corresponds to the population of Table 1 at various threshold energy density levels. An example population is given below in Table 2 wherein 2500 J/g is chosen for the energy density threshold level for the case wherein $\alpha_{site}=0.64$ Np/cm.

TABLE 2

| Energy Density Level = 2500 J/g | Positive Biopsy | Negative Biopsy |
|---|---|---|
| Below Energy Density Level | 13 | 2 |
| Above Energy Density Level | 1 | 3 |

Based on the values in Table 2, the false positive rate (1-specificity) and the true positive rate (sensitivity) are 0.40 and 0.93 respectively. By changing the threshold density of the energy deposition level additional data points for curve 404 may be obtained to complete curve 404.

The area under each curve 402, 404 is an indication of the applicability of the parameter being tested (density of the energy deposition) as a predictive factor. As background, for a case of random guessing, the resulting ROC curve is curve 406 which is a diagonal line from point (0,0) to (1,1) with an area under the curve of 0.5. In contrast, the area under the curve for a 'perfect' test is 1.0. This test has a decision level that produces a sensitivity of 1.0 with a specificity of 1.0 (i.e. no false positives and no false negatives). Turning to FIG. 7, the area under curve 402 corresponding to $\alpha_{site}=\infty$, is about 0.77 and the area under curve 404 corresponding to $\alpha_{site}=0.64$ Np/cm is about 0.80. Based on these areas, density of the energy deposition appears to be a strong predictor in the success or failure of a HIFU Treatment.

It should be noted that ROC analysis does not state what the decision level (in this case the threshold density of the energy deposition) should be, but rather only provides a measure of the usefulness of the test parameter, the density of the energy deposition. The threshold density of the energy deposition should be chosen based on balancing the cost of false positives (erroneously stating that the HIFU Treatment was a failure) versus false negatives (erroneously stating that the HIFU Treatment was a success).

Based on the sample data analyzed, an exemplary threshold density of the energy deposition resulting in a false negative rate of about 0 percent and a false positive rate of about 60 percent is at least about 3000 J/g (assuming infinite attenuation) and at least about 2800 J/g (assuming finite attenuation). Another exemplary threshold density of the energy deposition resulting in a false negative rate of about 29 percent and a false positive rate of about 40 percent is at least about 2700 J/g (assuming infinite attenuation). A further exemplary threshold density of the energy deposition resulting in a false negative rate of about 7 percent and a false positive rate of about 40 percent is at least about 2500 J/g (assuming finite attenuation). Yet another exemplary threshold density of the energy deposition is between about 2700 J/g and about 3000 J/g (assuming infinite attenuation). Still a further exemplary threshold density of the energy deposition is between about 2500 J/g and about 2800 J/g (assuming finite attenuation). Increasing the threshold density of the energy deposition results in a maximization of sensitivity. However, setting a threshold density of the energy deposition too high could result in a rise in the risk of adverse effects, such as rectal wall damage and/or the generation of undesirable hyperechoic features, such as non-focal hyperechoic features.

One of the benefits of using density of the energy deposition as a test for the success or failure for HIFU Treatments is the ability to ascertain the likelihood of the success of the HIFU Treatment prior to and/or during the administration of HIFU Therapy. As explained herein, the density of the energy deposition may be calculated for a proposed HIFU Treatment plan to provide the physician with a predictive indicator of the success of such treatment plan. Further, as explained herein, the density of the energy deposition may be calculated for a current HIFU Treatment to advise the physician with a predictive indicator of the success of such treatment plan.

The use of density of the energy deposition may be used as a guide to the physician during the planning portion of the HIFU Treatment (Does the proposed plan result in a density of the energy deposition at or above the chosen threshold density of the energy deposition?) and/or during the actual HIFU Treatment itself (Is the treatment on pace to result in a density of the energy deposition at or above the chosen threshold density of the energy deposition?).

Figure 8A:
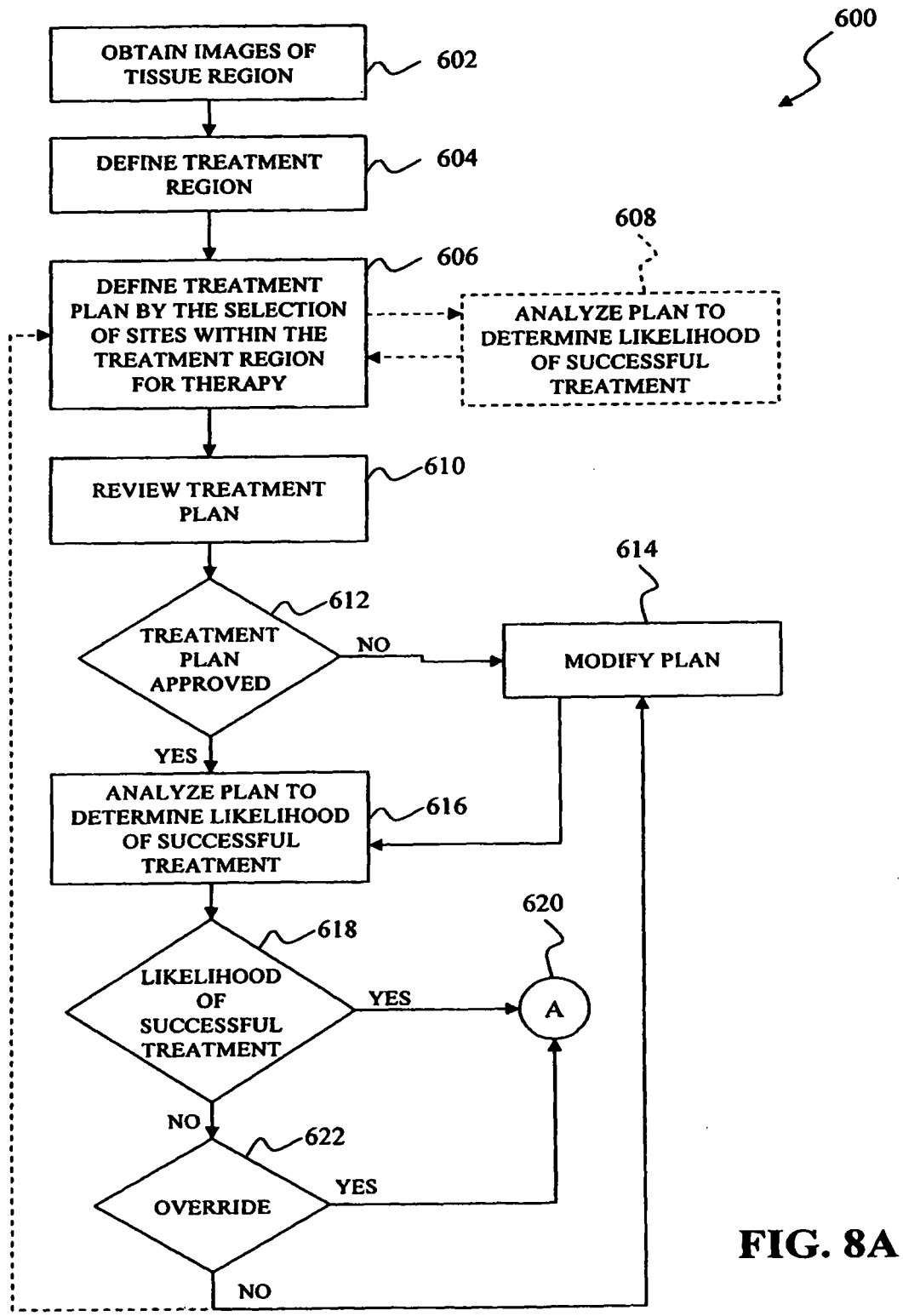
FIGS. 8A and 8B illustratively provide an exemplary method of operation of the HIFU System of FIG. 1 wherein the HIFU System analyzes a planned or proposed HIFU Treatment, a current HIFU Treatment, and/or a completed HIFU Treatment to predict the success of such HIFU Treatment.
Figure 8B:
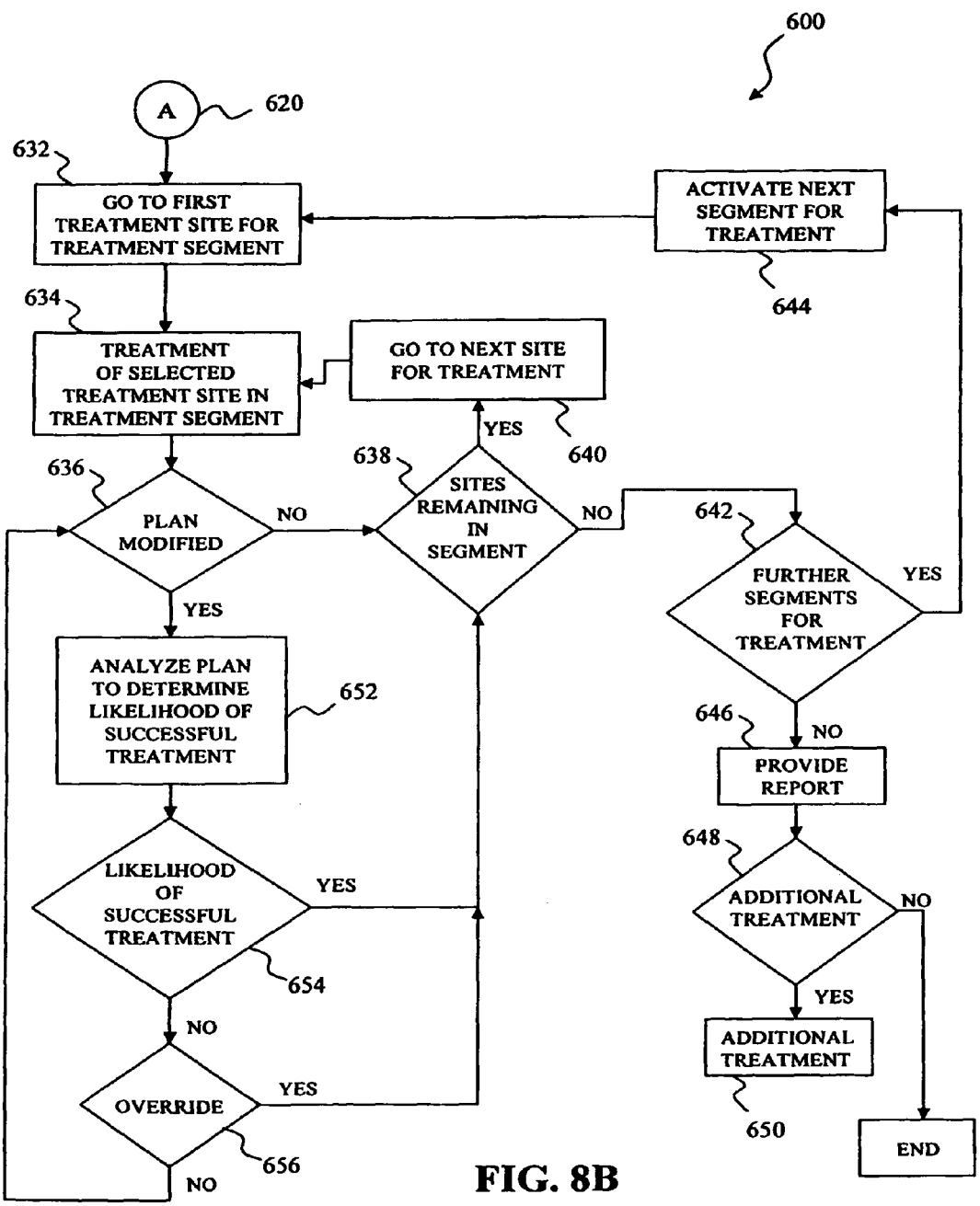

Referring to FIGS. 8A and 8B, an exemplary method of operation 600 of HIFU System 100 is provided, wherein HIFU System 100 uses the density of the energy deposition as a predictive factor to determine the likelihood of success of a given HIFU Treatment. Referring to FIG. 8A, once probe 102 has been properly positioned relative to the patient, images of tissue 10 are generated and stored, as represented by block 602. Exemplary methods of imaging tissue 10 are provided herein and in the various patents and patent applications incorporated by reference herein. Next, the treatment region 12 is defined, as represented by block 604. Exemplary methods of defining treatment region 12 are provided herein and in the various patents and patent applications incorporated by reference herein. As stated herein the treatment region may correspond to the overall prostate.

Once treatment region 12 has been defined, a treatment plan is generated including a plurality of sites within treatment region 12 which will be subject to HIFU Therapy, as represented by block 606. Exemplary methods of generating a treatment plan are provided herein and in the various patents and patent applications incorporated by reference herein. In one embodiment, the treatment plan is generated based on physician input of treatment segments to provide HIFU Therapy thereto. In this example, treatment sites are generated for each treatment segment, each treatment site corresponds to a location within the treatment segment which is the intersection of a transverse image and a longitudinal image.

In another embodiment, the treatment plan is generated automatically based on the 3-D model of tissue 10. In one example, various treatment segments are automatically selected each having a plurality of treatment sites. In one variation, the treatment segments and/or treatment sites are chosen to exclude certain tissue components from being subjected to HIFU therapy, such as the neuro-vascular bundle (NVB). As explained in U.S. Provisional Application Ser. No. 60/568,556, PCT Patent Application Serial No. US2005/015648, filed May 5, 2005, designating the U.S., titled "Method and Apparatus for the Selective Treatment of Tissue," the disclosures each of which is incorporated by reference herein, the locating of the NVB is accomplished in part through Doppler imaging of tissue 10.

In the case of automatic generation of the treatment plan, after the treatment plan has been generated the treatment plan is analyzed to determine the likelihood of success of the treatment plan, as represented by block 608. The energy expected to be deposited at each treatment site is summed and divided by the mass or volume of the treatment region to obtain the density of the energy deposition. As stated herein, the energy density may be computed for the overall treatment region and/or for various sub-components thereof, such as treatment segments. As such, the energy density may be used as a predictive factor for the overall treatment region and/or for the various sub-components thereof.

By determining the likelihood of success of the automatically generated treatment plan, HIFU System 100 is able to make sure that the automatically generated plan which is presented to the physician for approval should result in a successful HIFU Treatment. It should be understood, that if the treatment plan or portions of the treatment plan do not indicate a likelihood of success then the system automatically regenerates a new treatment plan which is analyzed to determine if the new plan is likely to result in a successful HIFU Treatment. This process is repeated until a treatment plan that is likely to result in success is generated. In one example, HIFU System 100 attempts a limited number of treatment plans before it prompts the user that a successful treatment plan cannot be generated.

It should be noted that various modifications may be made to an automatically generated treatment plan to increase the energy density value of the new automatically generated treatment plan. For example, the energy provided to one or more sites may be increased by lengthening the time that energy is provided ($t_{ON}$) and/or by increasing the total acoustic power at the site ($TAP_{site}$). In another example, the number of treatment sites is increased. In still another example, the number of treatment sites is increased and the energy provided to one or more sites is increased.

Once a treatment plan is generated, either with physician input on the treatment segments or automatically, (and in the case of automatic generation is analyzed to make sure that it is likely to result in a successful HIFU Treatment), the treatment plan is presented to the physician for review, as represented by block 610. In one embodiment, the physician reviews the plan by looking at the proposed treatment sites superimposed over various transverse and/or longitudinal images of the tissue 10 including the prostate. In another example, the physician reviews the plan by looking at the proposed treatment sites superimposed over a 3-D model of the tissue 10 including the prostate and/or various transverse and/or longitudinal images of the tissue 10 including the prostate.

Once the physician has reviewed the treatment plan, the physician may either approve the treatment plan or modify the treatment plan, as represented by block 612. There are various reasons why the physician may want to modify the treatment plan. In one example, the physician might want to exclude treatment sites too close to certain tissue components, such as the NVB, the urethra, the rectal wall, and/or the prostate capsule. In another example, the physician might want to add additional treatment sites. In yet another example, the physician may want to alter the total acoustic power ($TAP_{site}$) for various treatment sites or other parameters of the treatment plan. Regardless of the reasons, the physician has the ability to modify the treatment plan, as represented by block 614.

If the physician selected to approve the treatment plan, the treatment plan is analyzed to determine the likelihood of success of the treatment plan, as represented by block 616. It should be noted that if the physician is simply approving without modification a treatment plan that had previously been analyzed for success (block 608) then the treatment plan does not need to be again analyzed for success at block 616. However, if the treatment plan was not automatically generated and/or if the physician has made modifications to the treatment plan, regardless of whether the treatment plan had been previously analyzed, the treatment plan is analyzed to determine the likelihood of success of the treatment plan, as represented by block 616.

In one embodiment, to determine the likelihood of success of the treatment plan, the energy expected to be deposited at each treatment site is summed and divided by the mass or volume of the treatment region to obtain the density of the energy deposition. As stated herein, the energy density may be computed for the overall treatment region and/or for various sub-components thereof, such as treatment segments. As such, the energy density may be used as a predictive factor for the overall treatment region and/or for the various sub-components thereof. The calculated density of the energy deposition for the overall treatment plan or portions thereof is then compared to a reference density of the energy deposition. In one embodiment, the planned HIFU Treatment is considered to likely be successful if the calculated density of the energy deposition is equal to or exceeds the reference density of the energy deposition. In another embodiment, the probability of success may be computed based on the probability density functions constructed from the results of previous treatments. Exemplary reference density of energy depositions include at least about 2500 J/g, at least about 2700 J/g, at least about 2800 J/g, at least about 3000 J/g, between about 2500 J/g and about 2800 J/g, and between about 2700 J/g and about 3000 J/g.

If the treatment plan has a likelihood of success then HIFU System 100 begins the therapy portion, as represented by blocks 618 and 620. If the treatment plan does not have a likelihood of success then HIFU System 100 prompts the physician to determine if the physician wants to override software 109 and begin therapy, as represented by block 622. There might be several reasons why a physician would want to override the system and proceed with a therapy that according to the density of the energy deposition analysis is not likely to result in a successful treatment. For instance, the physician might have a need to keep the total acoustic power low based on the structure of the tissue; the tissue might include micro-calcifications in the prostate proximate to the rectal wall.

If the physician chooses to not override HIFU System 100, the physician is presented with the treatment plan and permitted to modify the treatment plan, as represented by block 614. In one embodiment, the physician is presented with the treatment plan as it currently exists. In another embodiment, wherein the treatment plan had been modified, the physician is presented with the treatment plan as it existed prior to any modification. In one example, the unmodified treatment plan is retrieved from memory. In another example, the unmodified treatment plan is regenerated, as represented by block 606.

Referring to FIG. 8B, an exemplary therapy routine 630 is shown. Therapy routine 630 is entered by either the approval of the treatment plan, as represented by block 618 in FIG. 8A, or by physician override, as represented by block 622 in FIG. 8A. Transducer 104 is positioned such that it is prepared to provide HIFU Therapy to the first treatment site in a given treatment segment, as represented by block 632. HIFU Therapy is then provided to the selected treatment site in the selected treatment segment, as represented by block 634.

Images of each treatment site are taken after the respective site has received HIFU Therapy. The physician monitors these images and may make changes to the treatment plan based on these images, as represented by block 636. For example, the physician may change the total acoustic power for subsequent treatment sites ($TAP_{site}$). The physician may alter the $TAP_{site}$ based on the images obtained after treatment. One reason the physician may alter the treatment is the generation of hyperechoic features after treatment.

Figure 9A:
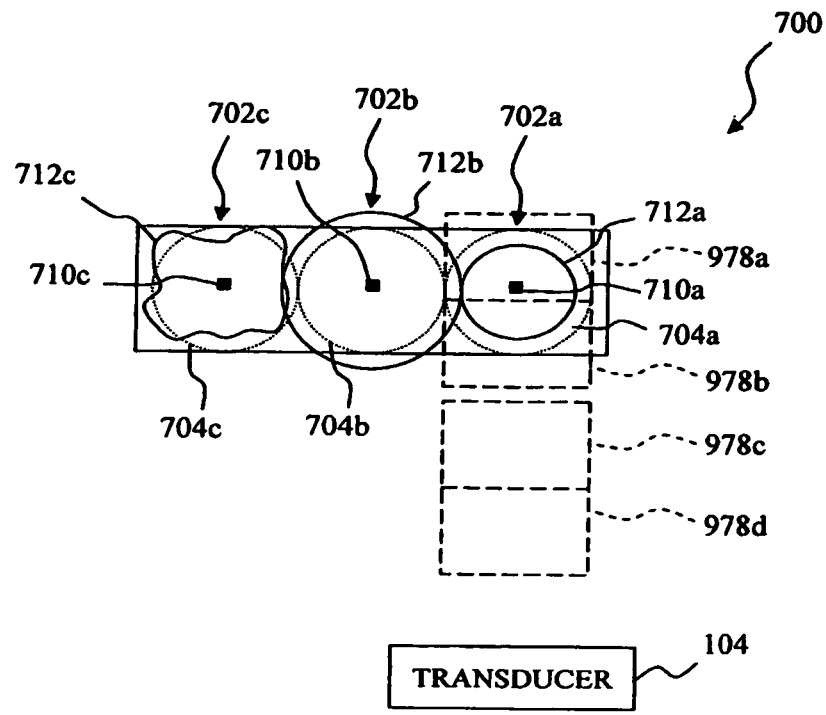
FIGS. 9A and 9B illustratively describe various hyperechoic features, including focal hyperechoic features and non-focal hyperechoic features.
Figure 9B:
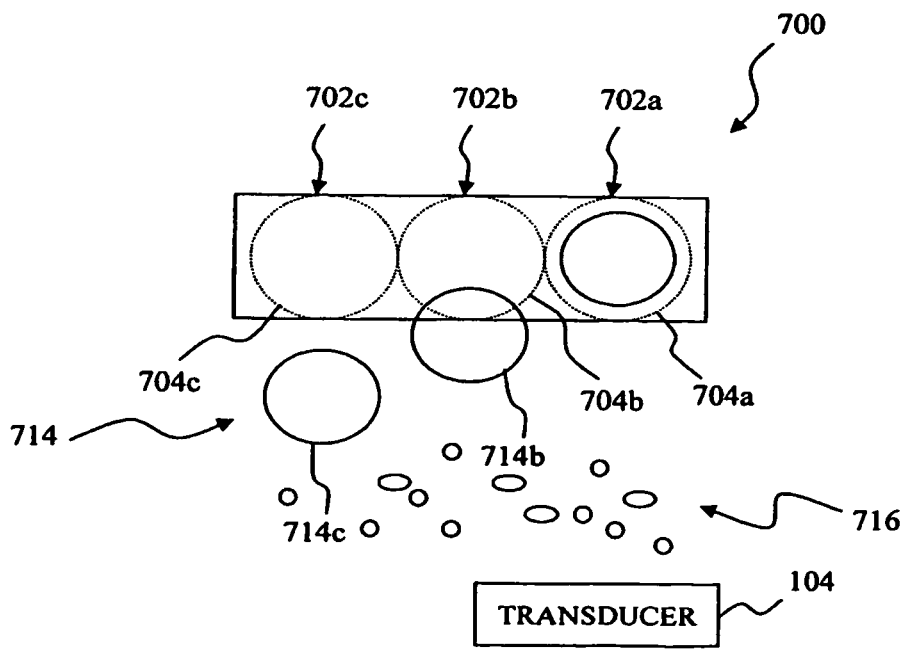

Referring to FIGS. 9A and 9B, an illustrative treatment region 700 is shown having three treatment sites 702a, 702b, and 702c. Each of the three treatment sites 702a-c include a focal zone 704a-c whereat ultrasound energy from transducer 104 is focused during a HIFU Therapy of the respective treatment site. In one embodiment, focal zone 704 has a volume of about 60 mm³ and a transverse width of about 3 mm.

As is well known, the focusing of the ultrasound energy at a treatment site 702 results in the raising of the temperature of the tissue in and proximate to the respective treatment site 702a, 702b, and 702c. By raising the temperature enough the unwanted tissue at the respective treatment site 702a, 702b, 702c is destroyed by ultrasound ablation. Further, it is known that at sufficient power levels that hyperechoic features may be generated. (See Sanghvi et al., "Noninvasive Surgery of Prostate Tissue by High-Intensity Focused Ultrasound," IEEE Transactions on Ultrasonics, Ferroelectrics, and Frequency Control (1996), the disclosure of which is incorporated by reference herein.)

Referring to FIGS. 9A and 9B, four types of hyperechoic features 710, 712, 714, 716 are shown. Each of FIGS. 9A and 9B generally illustrate an exemplary sector image of tissue 10. Hyperechoic feature 710 is confined to the respective focal zone 704 of the respective treatment site 702 and is therefore a focal hyperechoic feature. Further, hyperechoic feature 710 is generally smaller than the respective focal zone 704, such as a transverse extent of the focal zone or a depth of the focal zone (viewable in a corresponding longitudinal image). Hyperechoic feature 712 is substantially the same size as focal zone 704, such as a transverse extent of the focal zone or a depth of the focal zone, and is generally confined to focal zone 704. Hyperechoic feature 712 is an exemplary focal hyperechoic feature. In one example, hyperechoic feature 712a is slightly smaller than focal zone 704a. In another example, hyperechoic feature 712b is larger than focal zone 704b. In a preferred example adjacent hyperechoic features, such as hyperechoic feature 712a, 712b, substantially touch each other. Both hyperechoic feature 710 and 712 are desired hyperechoic features, with hyperechoic feature 712 being preferred.

Hyperechoic feature 714 is generally similar to hyperechoic feature 712 except that hyperechoic feature 714 is migrating from the focal zone 704 toward transducer 104, resulting in the treatment of tissue outside of focal zone 704. Such migration may result in the damage of tissue which would not otherwise be damaged, such as rectal wall 323. Hyperechoic feature 714 is generally site specific and therefore is an exemplary non-focal hyperechoic feature. For example, hyperechoic 714b and 714c are each generally in line with their respective treatment sites, 704b and 704c.

In contrast, hyperechoic feature 716 is not site specific. Hyperechoic feature 716 corresponds to the formation of a cloud of multiple bubbles across the tissue in the area between transducer 104 and treatment region 700 due to the overall heating of tissue 10. Hyperechoic feature 716 blocks the HIFU energy from reaching treatment region 200 for successive treatment sites 702. Examples of hyperechoic features 716 are discussed in the paper Sanghvi et al., "Noninvasive Surgery of Prostate Tissue by High-Intensity Focused Ultrasound," IEEE Transactions on Ultrasonics, Ferroelectrics, and Frequency Control (1996), the disclosure of which is incorporated by reference herein. In one embodiment, if hyperechoic feature 714 or hyperechoic feature 716 are detected the HIFU Treatment should be paused and/or the $TAP_{site}$ reduced.

The physician may reduce the $TAP_{site}$ if hyperechoic features are visible in the images, to prevent the formation of non-focal hyperechoic features, or in order to maintain focal hyperechoic features. The physician may increase $TAP_{site}$ to bring about the occurrence of focal hyperechoic features. Further, the physician may pause the HIFU Treatment due to the presence of non-focal hyperechoic features or clouds of micro bubbles. In addition, the physician may stop the HIFU Treatment.

Figure 10:
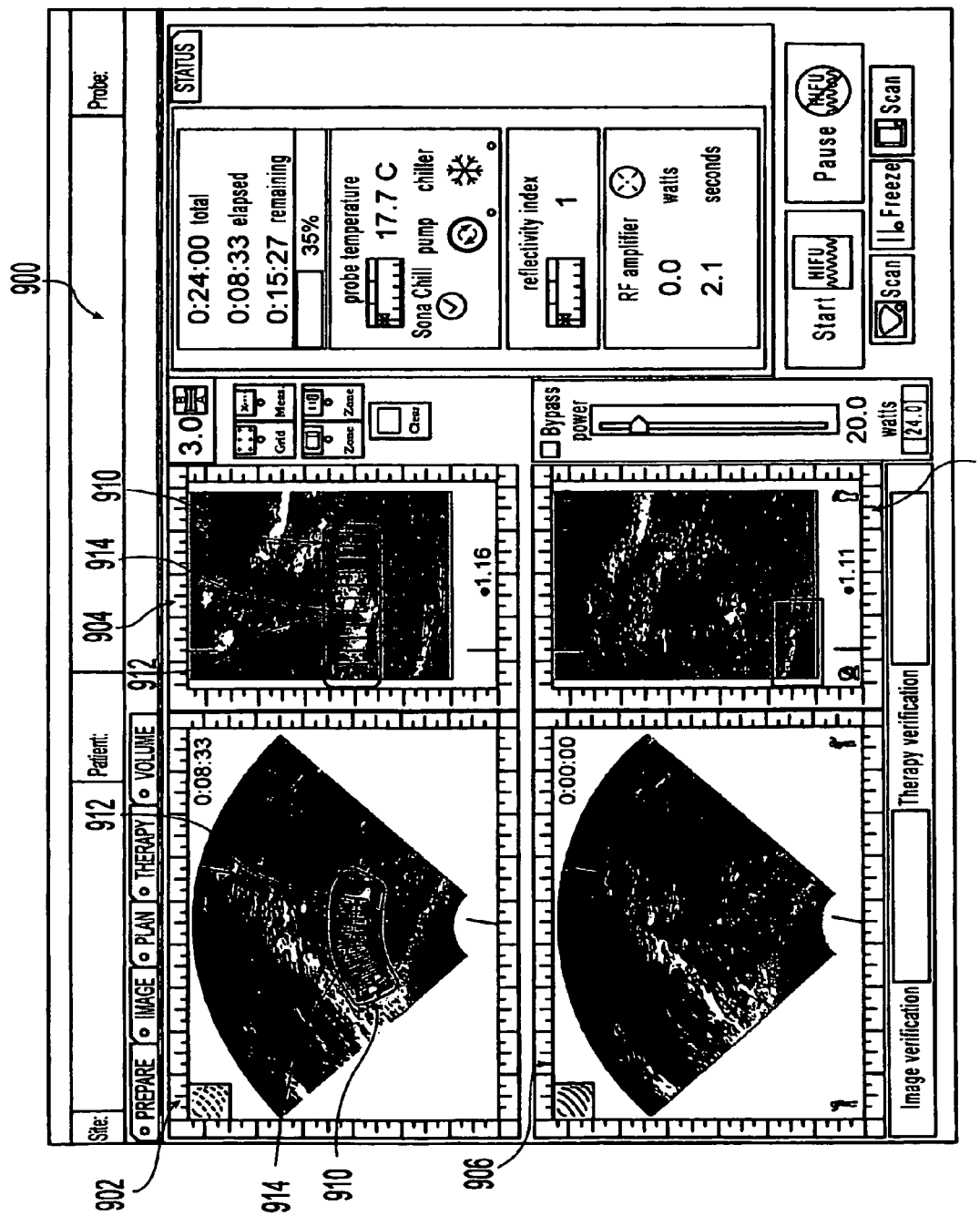
FIG. 10 illustrates exemplary focal hyperechoic features.

Referring to FIG. 10, wherein HIFU System 100 is based on the Sonablate® 500 HIFU System available from Focus Surgery located in Indianapolis, Ind., an exemplary partial screenshot 900 of display 111 is shown. Shown are pre-treatment images (transverse and longitudinal) 906 and 908 of tissue 10 and post-treatment images (transverse and longitudinal) 902 and 904 of tissue 10. Post-treatment images 902 and 904 include a representation 910 of the various treatment sites 912. As seen in each of images 902 and 904, a bright echo is observed generally confined to the region of treatment site 912. Such bright echo is a focal hyperechoic feature 914.

Figure 11:
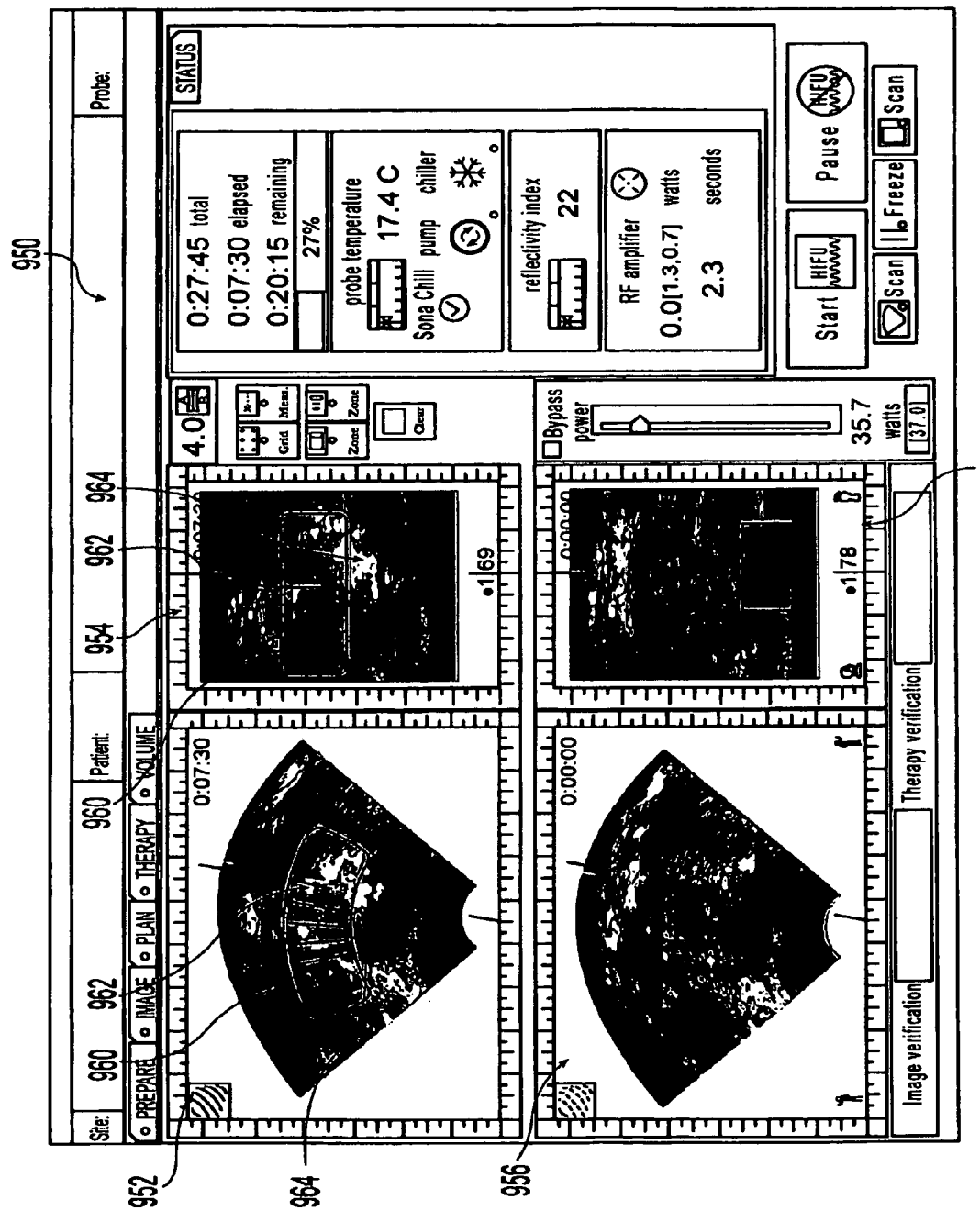
FIG. 11 illustrates exemplary non-focal hyperechoic features.

Referring to FIG. 11, wherein HIFU System 100 is the Sonablate® 500-PC apparatus available from Focus Surgery located in Indianapolis, Ind., an exemplary partial screenshot 950 of display 111 is shown. Shown are pre-treatment images (transverse and longitudinal) 956 and 958 of tissue 10 and post-treatment images (transverse and longitudinal) 952 and 954 of tissue 10. Post-treatment images 952 and 954 include a representation 960 of the various treatment sites 962. As seen in each of images 952 and 954, a bright echo is observed generally in front of the region of treatment site 962, but generally confined to the region of tissue that energy was applied to during the HIFU Therapy of treatment site 962. Such bright echo is a non-focal hyperechoic feature 964.

Returning to FIG. 8B, if changes are not made to the treatment plan then it is determined if additional untreated treatment sites remain in the treatment segment, as represented by block 638. If additional untreated treatment sites remain in the treatment segment, then transducer 104 is positioned to provide HIFU Therapy to the next treatment site, as represented by block 640. HIFU Therapy is provided to the next treatment site, as represented by block 634. If additional untreated treatment sites do not remain in the treatment segment, then a determination is made whether there are additional untreated treatment segments in the treatment plan, as represented by block 642. If there are additional untreated treatment segments, the next treatment segment is activated, as represented by block 644 and transducer 104 is positioned to provide treatment to the first treatment site of the new treatment segment as represented by block 632. If there is not any additional untreated treatment segments, the HIFU Treatment is completed and the physician is provided with a report, as represented by block 646.

In one embodiment, the report includes a statement on whether the treatment was likely to be successful. This is based on comparing the resulting density of the energy deposition to the set threshold value. In another embodiment, the report includes a probability of success for the treatment. This probability is based on a library accessible by controller 108 containing the outcome for numerous previous treatment and the associated density of the energy deposition.

In one embodiment, a final analysis of the treatment plan is conducted and is included in the report. The final analysis includes at least an indicator of the likelihood of success of the HIFU Treatment, such as the density of the energy deposition of the HIFU Treatment. In one example, the density of the energy deposition is given for the individual treatment segments and/or the overall treatment plan. Based on the report, the physician may decide to return to various treatment segments to provide additional HIFU Therapy to one or more treatment sites in the treatment segment, as represented by blocks 648 and 650.

Returning to block 636, if the physician decides to modify the treatment plan during the HIFU Treatment the modified treatment plan is analyzed to determine the likelihood that it will produce a successful HIFU Treatment, as represented by block 652. In one embodiment, the modified treatment plan is evaluated using the density of the energy deposition discussed herein. The density of the energy deposition is calculated by summing the energy deposited at all the previously treated treatment sites and by summing the energy to be deposited at the remaining treatment sites of the current treatment region with the assumption that the current TAP level will be used for all remaining treatment sites.

In one embodiment, HIFU System 100 provides a visual cue on display 112 to the physician, the visual cue providing an indication of whether the current HIFU Treatment should likely be a successful HIFU Treatment. In one example, the visual cue is a marker that is positioned along a bar with shades of red, yellow, and green that represent respectively a low, medium and high likelihood of success of the HIFU Treatment.

If the modified treatment will likely result in a successful treatment, then transducer 104 is moved to the next treatment site to be treated, as represented by blocks 654 and 638. If the modified treatment plan is not projected to result in a successful treatment then the user may override HIFU System 100, as represented by block 656. If the user does not override HIFU System 100, the user is again presented with the option to modify the treatment plan, as represented by block 636. If the user does override HIFU System 100, transducer 104 is moved to the next treatment site to be treated, as represented by block 638.

In one embodiment, the physician may decide to override HIFU System 100 if the physician is seeing on the images subsequent to treatment, a focal hyperechoic feature and the physician wants to lower the TAP at future treatment sites to maintain such focal hyperechoic features. In another embodiment, the physician may decide to override HIFU System 100 and reduce the $TAP_{site}$ to prevent the formation of non-focal hyperechoic features or clouds of micro bubbles.

Figure 12:
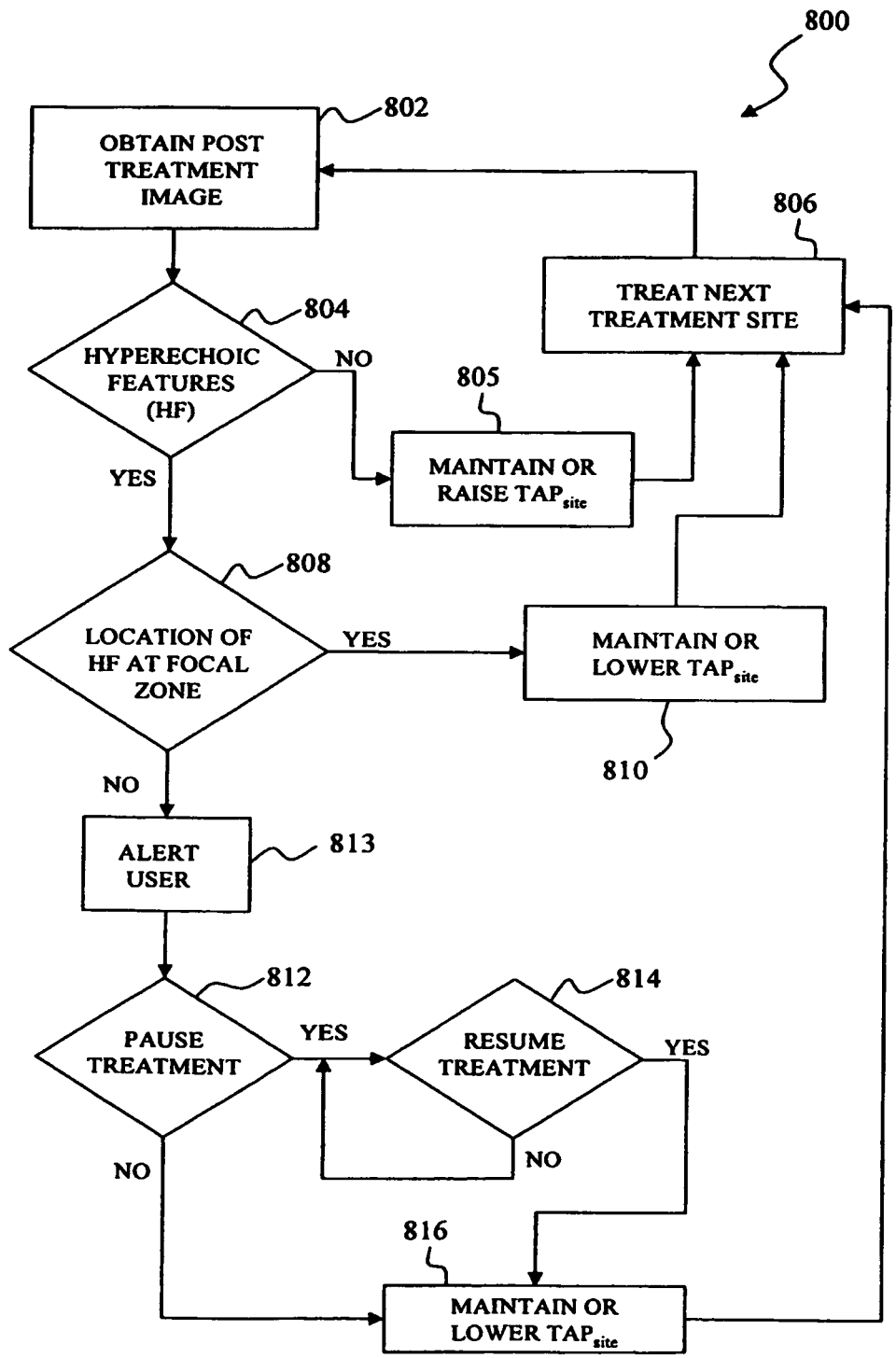
FIG. 12 illustratively provides an exemplary method of tailoring the treatment of tissue based on the presence of hyperechoic features.

In one embodiment, HIFU System 100 monitors the images taken subsequent to treatment and makes a determination of the presence or absence of various hyperechoic features. Referring to FIG. 12, an exemplary method of operation 800 of HIFU System 100 for such monitoring is shown. HIFU System 100 obtains post treatment images of the treatment site just treated with HIFU Therapy, as represented by block 802. The images are analyzed to determine the presence of hyperechoic features, as represented by block 804. In one example, HIFU System 100 compares the post treatment images to images representative of various hyperechoic features stored in image library 111. In one example, image library 111 contains examples of focal hyperechoic feature 710, focal hyperechoic feature 712, non-focal hyperechoic feature 714, and clouds of micro bubbles 716. Various image processing techniques, such as measuring the change in the average image intensity in the image as a whole and/or in a portion of the image corresponding to the treatment site and/or to the region in front of the treatment site, may be used to compare the images.

If hyperechoic features are not present in the post treatment images, the next treatment site to be treated with HIFU Therapy is treated, as represented by block 806. If hyperechoic features are present in the post treatment images, a determination is made of whether the hyperechoic features are focal hyperechoic features, the hyperechoic features are non-focal hyperechoic features, or the hyperechoic features are clouds of micro bubbles, as represented by block 808. If the hyperechoic features are focal hyperechoic features, then the $TAP_{site}$ for the next treatment site is either maintained or lowered slightly, as represented by block 810. In one example, the determination of whether to maintain or lower the $TAP_{site}$ is automatically made based on changes in the image intensity or signal intensity corresponding to the treatment region before and after application of HIFU Therapy at the treatment site. An increase of the image intensity beyond a set threshold for signals arriving from before the treatment region would indicate the need to reduce the $TAP_{site}$. In another example, the physician is prompted to make the determination of whether to maintain or lower the $TAP_{site}$.

If the hyperechoic features are non-focal hyperechoic features, then the decision is made whether the HIFU Treatment should be paused, as represented by block 812. In one example, this determination is automatically made. In another example, the physician is prompted, as illustrated by block 813, to make the determination of whether to pause the HIFU Treatment. HIFU System 100 then waits until a decision is made to resume treatment as represented by block 814. In one example, the decision to resume treatment is automatically made. In another example, the physician is prompted to make the determination of whether to resume the HIFU Treatment. If the treatment is resumed or the decision was made to not pause the treatment, then the $TAP_{site}$ is lowered and the next treatment site is treated, as represented by blocks 816, 806. In one example, the reduction in the $TAP_{site}$ is automatically made. In another example, the physician is prompted to reduce the $TAP_{site}$.

In one embodiment, based on the detection of focal hyperechoic features, HIFU System 100 automatically lowers or maintains the $TAP_{site}$ for subsequent treatment sites to maintain such focal hyperechoic features. In one embodiment, based on the detection of non-focal hyperechoic features, HIFU System 100 automatically lowers the $TAP_{site}$ for subsequent treatment sites and/or pauses the HIFU Treatment.

Figure 16:
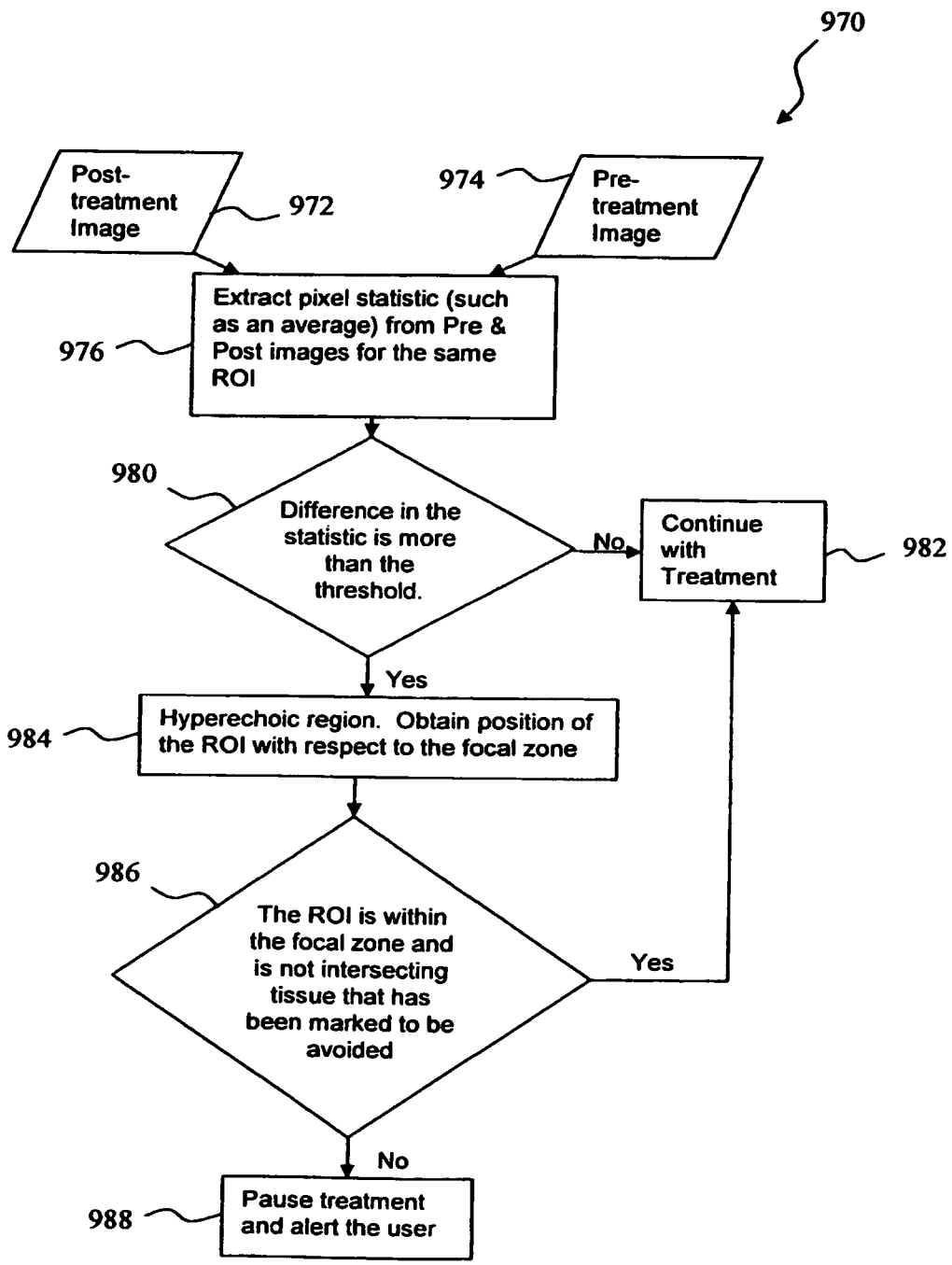
FIG. 16 is an exemplary method for detecting and classifying hyperechoic features.

Referring to FIG. 16, an exemplary method 970 is provided for determining if a hyperechoic feature is present relative to a given treatment site and to classify the hyperechoic feature as one of a focal hyperechoic feature or a non-focal hyperechoic feature. As represented by block 972 a post-treatment image containing the treatment site is obtained with HIFU System 100. Further, a pre-treatment image containing the treatment site is obtained with HIFU System 100, as represented by block 974. In one embodiment, the pre-treatment image containing the treatment site is retrieved from image library 111 or other memory accessible by controller 108. Next, an image characteristic is determined for a given region of interest ("ROI") for each of the pre-treatment image and the post-treatment image, as represented by block 976. In one embodiment, the ROI generally corresponds to the same tissue location in both the pre-treatment image and the post-treatment image. Exemplary image characteristics include an average pixel intensity, standard deviation of pixel intensity, geometric mean of the pixel intensity, root-mean-square of the pixel intensity. In one example, an average pixel intensity is used for the image characteristic.

Referring to FIG. 9A, exemplary ROIs 978a, 978b, 978c, and 978d are shown. ROIs 978 are illustratively shown as being generally quadrilaterally shaped, but may be any desired shape. ROIs 978a and 978b are generally confined to treatment site 702a and thus generally correspond to the detection of focal hyperechoic features. ROIs 978c and 978d are generally positioned in line with transducer 104 and treatment site 702a and are forward of treatment site 702a and thus generally correspond to the detection of non-focal hyperechoic features. Although four ROIs are shown for illustrative purposes, more or less ROIs may be implemented.

Returning to FIG. 16, for a given ROI a comparison between the image characteristic for the corresponding pre-treatment ROI and the corresponding post-treatment ROI, as represented by block 980. In the illustrated embodiment, a difference is determined between the post-treatment average pixel intensity and the pre-treatment average pixel intensity. This difference is compared to a threshold value stored by controller 108, as represented by block 980.

If the difference is less than the threshold value, treatment is continued as represented by block 982. In one embodiment, treatment is continued after all ROIs to be analyzed for the given treatment site have been analyzed by the method illustrated in FIG. 16. In one example, this includes non-focal ROIs such as 978*c* and 978*d* and focal ROIs such as 978*a* and 978*b*. If the difference meets or exceeds the threshold value then the position of the given ROI relative to the focal zone or location of treatment site 702*a* is determined, as represented by block 984. If the given ROI is positioned within the focal zone or generally within treatment site 702*a*, treatment is continued as represented by blocks 986 and 982. If the given ROI is positioned outside of the focal zone or generally outside treatment site 702*a*, the treatment is paused and the physician is alerted, as represented by block 988.

Further, in one embodiment, a further analysis is performed prior to permitting treatment to continue. In the illustrated embodiment, a further analysis is performed to determine if the ROI corresponds to tissue that has been marked to be excluded from treatment as discussed herein, such as NVBs, or simply the location of the ROI relative to the treatment region, such as within the focal zone, before the focal zone, within the rectal wall, and outside the prostatic capsule. If the ROI does not correspond to tissue marked for exclusion from treatment, treatment is permitted to continue, as represented by block 982. If the given ROI corresponds to tissue marked for exclusion from treatment or is positioned outside of the focal zone or generally outside treatment site 702*a*, treatment is paused and the physician is alerted, as represented by block 988.

In one embodiment, HIFU System 100 is further configured to detect the presence of acoustic obstructions in the propagation path of the HIFU energy which are not generated as a result of the HIFU Treatment (not hyperechoic features). In the case of treating the prostate, exemplary acoustic obstructions 820 (see FIG. 3B) include air bubbles between probe 102 and rectal wall 323 or calcifications in the rectal wall itself. The presence of an acoustic obstruction blocks or at least severely limits the amount of HIFU energy that may proceed to the proposed treatment site during a HIFU Therapy. Similarly, the presence of an acoustic obstruction blocks or severely limits the amount of ultrasound energy that may penetrate beyond the obstruction to image the tissue behind the obstruction. As such, the acoustic obstruction may both limit the imaging ability of HIFU System 100 and limit the effectiveness of HIFU Therapy provided by HIFU System 100. Further, in the case of HIFU Therapy tissue proximate to the obstruction may be unintentionally damaged by the application of HIFU energy, such as rectal wall 323.

One method of detecting the presence of an acoustic obstruction is to analyze an image for one or more repetitive patterns of received acoustic signals. As is known, in ultrasound imaging an acoustic signal is transmitted into a medium and portions of the ultrasound signal are reflected back from portions of the medium and received by a transducer. The magnitude of these reflections are due to the properties of the portions of the medium causing the reflection. In the case of an acoustic obstruction proximate to the transducer, the acoustic signal is largely reflected by the acoustic obstruction back to the transducer. A portion of this large reflected signal is reflected by the transducer back into the medium wherein it is again reflected by the acoustic obstruction. This bouncing of the acoustic signal back-and-forth between the acoustic obstruction and the transducer generates a generally periodic acoustic signal in time at intervals corresponding to the distance between the transducer and the obstruction. This repetitive pattern may be used to detect the presence of the acoustic obstruction.

Figure 13A:
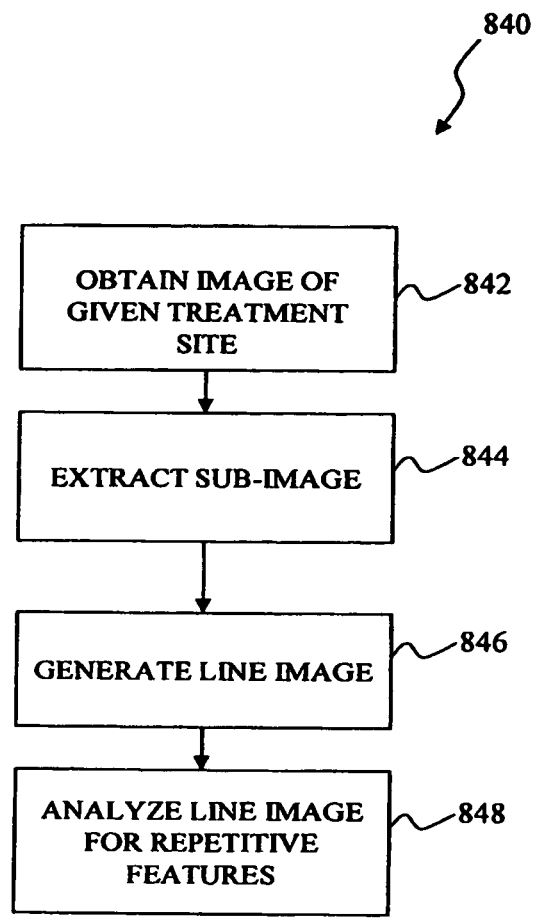
FIG. 13A illustratively provides an exemplary method of monitoring for acoustic obstructions proximate to the transducer relative to the treatment region and for tailoring the treatment of tissue based on the presence of the acoustic obstructions.
Figure 13B:
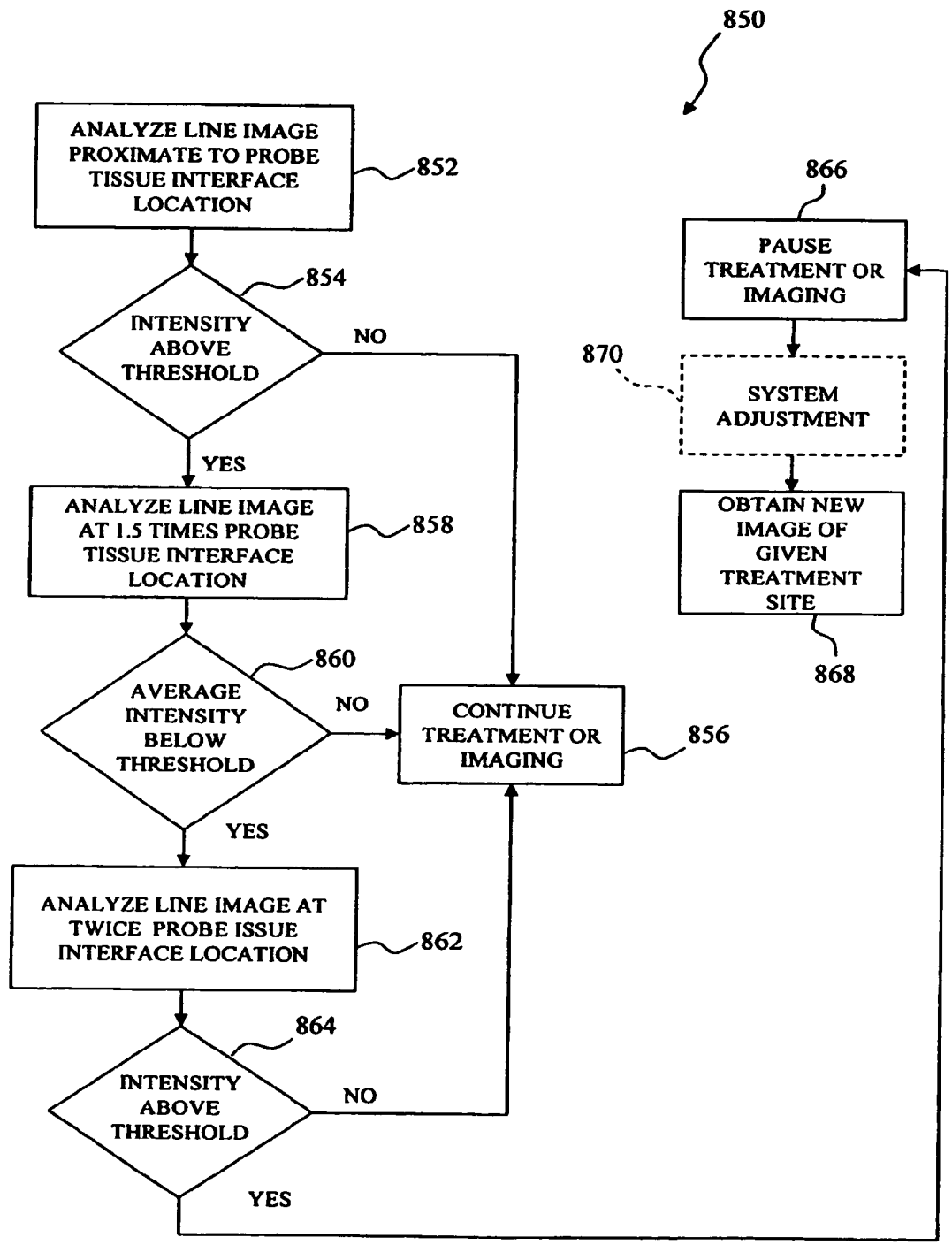
FIG. 13B illustratively provides an exemplary method of monitoring for acoustic obstructions by monitoring for repetitive acoustic features.

Referring to FIG. 13A, an exemplary method of operation 840 of HIFU System 100 for monitoring for acoustic obstructions is shown. HIFU System 100 obtains an image of the treatment site, as represented by block 842. The image may be a two-dimensional linear image or a two-dimensional sector image and may be a pre-treatment image or a post treatment image. In one embodiment, the exemplary methods provided in FIGS. 13A, 13B are included in software 109 of HIFU System 100. In one embodiment, obstruction routine 840 is automatically implemented for all imaging of the treatment region 12 including pre-treatment images and post-treatment images.

Once the image has been obtained, a portion or sub-image is extracted from the image which generally corresponds to either a proposed treatment site or a treatment site that has just been treated or attempted to be treated with HIFU energy, as represented by block 844. In one embodiment, the image and hence the sub-image correspond to an on-axis configuration between transducer 104 and the given treatment site. The sub-image is chosen to correspond to the lines or columns of pixels that generally correspond to the extent of the treatment site (in the case of a sector image generally the width of the focal zone of the transducer at the treatment site). In one example, wherein the focal width is about 3 mm and there are 4 pixels/mm, twelve columns or lines are in the extracted sub-image. The intensity values of the corresponding pixels in each line or column are averaged to produce a line image which provides the averaged intensity value as a function of time (depth from the transducer). This line image is then analyzed to determine if an acoustic obstruction is likely present, as represented by block 848. In one embodiment, the line image is analyzed to determine if it contains repetitive features.

Figure 14A:
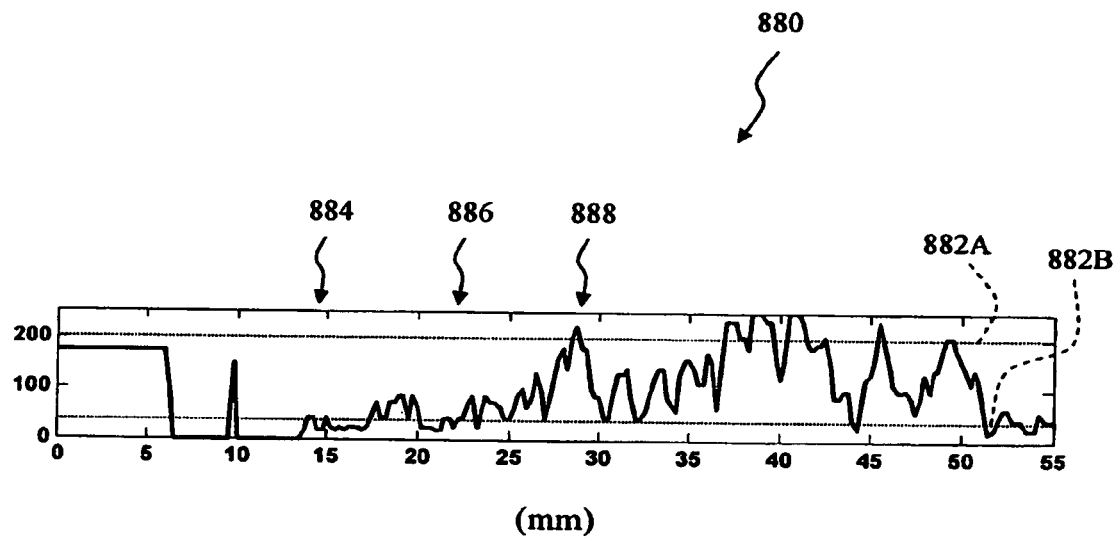
FIG. 14A is an exemplary line image of a portion of a treatment region including the rectal wall and prostate and not including an acoustic obstruction proximate to the transducer.
Figure 14B:
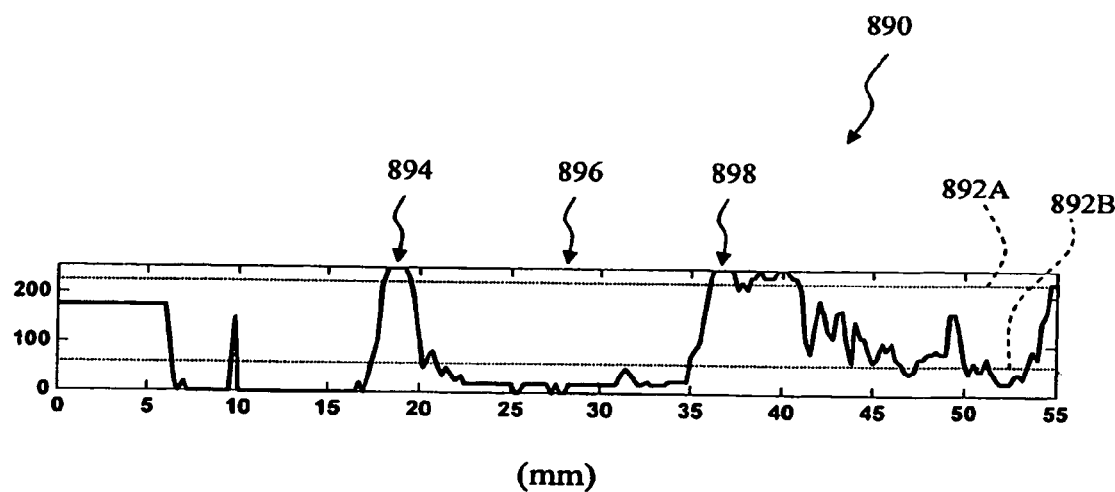
FIG. 14B is an exemplary line image of a portion of a treatment region including the rectal wall and prostate and including an acoustic obstruction proximate to the transducer.

An illustrative method 850 of analyzing the line image to determine if it contains repetitive features indicating an acoustic obstruction is provided in FIG. 13B. Method 850 is illustratively shown to detect the presence of an acoustic obstruction proximate to a probe/tissue interface, such as an interface between acoustic membrane 103 and rectal wall 323, during the imaging and/or the treatment of the prostate wherein probe 102 is inserted into rectum 322. An exemplary line image 880 generated from an image without an acoustic obstruction is shown in FIG. 14A. An exemplary line image 890 generated from an image having an acoustic obstruction is shown in FIG. 14B. Exemplary acoustic obstructions include air bubbles between probe 102 and rectal wall 323 and calcification of rectal wall 323.

In one embodiment, each of images 880 and 890 are normalized to intensity values ranging from 0 to 255. Illustratively shown in FIGS. 14A and 14B are upper and lower threshold lines 882A, 882B for image 880 and upper and lower threshold lines 892A, 892B for image 890. In one embodiment, the value for upper threshold 882A, 892A is set to 210 or about 82% of the scale and the value for lower threshold 882B, 892B is set to 50 or about 20% of the scale. Further, shown in each image 880, 890 are depths 884, 894 which generally correspond to the location of an interface between acoustic membrane 103 and rectal wall 323, depths

886, 896 which generally correspond to 1.5 times the location of the interface between acoustic membrane 103 and rectal wall 323, and depths 888, 898 which generally correspond to twice the location of the interface between acoustic membrane 103 and rectal wall 323.

Referring to image 880, prior to region 884 which generally corresponds to the interface between acoustic membrane 103 and rectal wall 323, two high intensity features are shown. Each of these features are artificial markers placed on the image from which image 880 is generated and do not correspond to acoustic features in the treatment region.

In one embodiment, image 880 is analyzed to determine if an intensity value associated with depth 884 exceeds or meets a first upper threshold, such as 882A, if an intensity value associated with depth 886 is below a first lower threshold, such as 882B, and if an intensity value associated with depth 888 exceeds or meets a second upper threshold. If the above three conditions are satisfied, an acoustic obstruction is detected at the probe/tissue interface, such as between acoustic membrane 103 and rectal wall 323. If one or more of the above three conditions are not satisfied, an acoustic obstruction is not detected at the probe/tissue interface, such as between acoustic membrane 103 and rectal wall 323. In one example, the second upper threshold is not equal to the first upper threshold. In another example, the second upper threshold is equal to the first upper threshold.

Returning to FIG. 13B, each of line images 880, 890 are analyzed for purposes of illustrating method 850. As represented in block 852, the respective line image 880, 890 is analyzed in the region proximate to the probe/tissue interface, such as between acoustic membrane 103 and rectal wall 323, respective regions 884, 894.

In one embodiment, the probe/tissue interface (depth location along line image 880, 890) is determined through image processing of the linear image 880, 890. The first step is to estimate the noise floor which is defined as a percentage of the average signal within a portion of the linear image 880, 890 or an image from which the respective linear images 880, 890 is generated. In one example, the noise floor is about 60% of the average intensity of the linear image 880, 890. Next, the probe/tissue interface is defined as the location at which the pixel intensity surpasses this noise floor. In another embodiment, the user is queried to indicate the location of the probe/tissue interface on the respective linear image 880, 890 or the image from which the respective linear image 880, 890 is generated. In one example, the user is prompted through display 112 and provides an indication of the location of the probe/tissue interface on the image through an input with input device 110.

In one embodiment, the noise floor is based on a portion or sub-image of the image that linear image 880, 890 is extracted from, in particular the portion extends from the position of the transducer to half the total depth of the image and across the central section of the columns of the image. In one example, the portion corresponds to about 126 pixels in depth for an image which is about 6.3 cm deep at 4 pixels/mm and about ninety columns from the central section of the image with about 45 columns on each side thereof. In another embodiment, the portion or sub-image that forms the basis of the noise level estimation may cover other areas of the image including the whole image. Further, the portion or sub-image may include one or more non-contiguous portions, such as every Nth column from a start column to a stop column. In one example, every third column from a start column at 1 and a stop column at 180. Further, the non-contiguous portions may also be in depth, such as every Mth pixel in depth from a depth of 0 mm until a stopping depth. In one example, M=3 with stopping depth at maximum depth of 63 mm.

Regardless of the portions of the image used to determine the average for the noise level, the noise level is a percentage of this average, such as about 60% of this average. Starting at a depth position of 0 mm test each pixel until the intensity is greater than the noise level it should be noted that the average intensity calculations and the test for the probe/tissue interface excludes the artifacts added to the image near the transducer, as discussed herein. This position is defined as the probe/tissue interface or in the case of treating the prostate, the rectal wall position. The average rectal wall position for the linear image is computed and is displayed for the user.

In another embodiment, the noise level is defined as discussed above, but the probe/tissue interface, the rectal wall position, is determined for a given treatment site as follows. The image lines (columns) pertaining to a treatment site (for example 3 mm with 4 pixels/mm resulting in 12 image lines) are extracted. The probe/tissue interface is found for each image line by determining the first pixel value in depth from the transducer exceeds the noise level and the average probe/tissue interface location based on the twelve line images is used for the rectal wall distance at this treatment site.

In one embodiment, the values of the pixels in respective regions 884, 894 are averaged to distinguish noise from acoustic features, determine the noise level. In one embodiment, this averaging is not triggered for the respective image unless at least one pixel value is above the respective upper threshold 882A, 892A. Referring to FIG. 14A, the pixels in region 884 each have an intensity value below upper threshold 882A thus indicating that a strong acoustic reflector or obstruction is not present in region 884. Referring to FIG. 14B, several of the pixels in region 894 have intensity values above upper threshold 892A indicating that a strong acoustic reflector or obstruction is potentially present in region 894. As such, a first check is whether the pixels in respective region 884, 894 are above the respective upper threshold 882A, 892A, as represented by block 854. In the case of image 880, the intensity values in region 884 are less than upper threshold 882A and hence treatment or imaging is continued as represented by block 856. In the case of image 890, the intensity values in region 894 exceed upper threshold 892A and hence additional analysis is performed.

The next region to be analyzed is region 896 generally corresponding to about 1.5 times the probe/tissue interface, as represented by block 858. Since the majority of the acoustic energy was reflected by an acoustic obstruction proximate to rectal wall 323 a small intensity value in region 896 should be observed because little to no acoustic energy is entering the tissue and thus reflections from deeper features beyond the rectal wall 323 are indistinguishable from noise. In contrast, referring to FIG. 14A, in image 880 intensity values greater than lower threshold 882B due to deeper acoustic features are observed in region 886. As such, a second check is to see if the intensity values in region 896 are below lower threshold 892B, as represented by block 860. If the intensity values exceed the lower threshold 892B then treatment or imaging is allowed to continue, as represented by block 856. In the case of image 890 the intensity values are less than lower threshold 892B and hence additional analysis is conducted.

The next region to be analyzed is region 898 generally corresponding to about twice the probe/tissue interface, as represented by block 862. Assuming the acoustic energy is bouncing between transducer 104 and the acoustic obstruction another bright echo (high intensity) should be present at region 898 if an acoustic obstruction is present. In one embodiment, the values of the pixels in region 898 are averaged to distinguish noise from acoustic features. In one embodiment, this averaging is not triggered unless at least one pixel value is above upper threshold 892A. Referring to FIG. 14B, several of the pixels in region 898 have intensity values above upper threshold 892A. If the intensity values did not exceed upper threshold 892A, treatment or imaging would be allowed to continue, as represented by block 856. However, the intensity values in region 898 exceed upper threshold 892A indicating the presence of an acoustic obstruction. In response, HIFU System 100 pauses imaging or treatment due to the presence of an acoustic obstruction, as represented by block 866.

At this point HIFU System 100 may either simply wait a predetermined time followed by an attempt to re-image the portion of treatment region 12, as represented by block 868 or permit system adjustment, as represented by block 870. Some types of acoustic obstructions, such as air bubbles introduced during the insertion of probe 102 or generated by patient flatulence, are transient acoustic obstructions. Other types of acoustic obstructions, such as calcification in the rectal wall 323, are generally permanent acoustic obstructions.

In the case of transient acoustic obstructions, the acoustic obstruction may migrate away from the probe 102 or may be removed by moving the probe 102 or by direct physician intervention. In the case of permanent acoustic obstructions, either the patient is not considered a good candidate for HIFU Treatment or the obstructed portion of treatment region 12 is simply not treated with HIFU Therapy. In one embodiment, wherein a phased array transducer is used, the obstructed portion of treatment region 12 may be treated by translating the transducer or activating a spaced apart aperture of the transducer and treating the obstructed portion from an off-axis position. An exemplary phased array transducer is provided in U.S. patent application Ser. No. 11/070,371, filed Mar. 2, 2005, the disclosure of which is expressly incorporated by reference herein.

Many of the methods described herein are based on or otherwise utilize the intensity values of one or more pixels in one or more images to detect acoustic features, classify acoustic features, and/or to make one or more treatment decisions. The intensity values of the pixels in the one or more images are based on the electrical radio frequency signals generated by the transducer in response to detected acoustic energy. As such, in one embodiment, the herein described methods may be based on the radio frequency signals themselves or various conditioned forms thereof instead of the intensity values of image pixels.

Although the invention has been described in detail with reference to certain illustrated embodiments, variations and modifications exist within the spirit and scope of the invention as described and defined in the following claims.

The invention claimed is:

1. A method of providing treatment to a treatment region of tissue, the method comprising:
   providing a system comprising a monitor, a surgical tool having a ultrasound transducer, and a processor, the ultrasound transducer being configured to provide imaging of the treatment region and administer high intensity focused ultrasound ("HIFU") Treatment;
   positioning the ultrasound transducer proximate to tissue of the treatment region;
   the processor being programmed to perform the steps of:
   generating a visual representation of the tissue on the monitor;
   identifying an ultrasound treatment site on the treatment region from the visual representation of the tissue;
   calculating a proposed ultrasound energy density for a proposed HIFU Treatment, wherein the energy density for the proposed HIFU Treatment is calculated by estimating an amount of energy to be deposited at the ultrasound treatment site and dividing the amount of energy to be deposited by one of a volume of the treatment region and a mass of the treatment region;
   comparing the calculated ultrasound energy density for the proposed HIFU Treatment to a reference ultrasound energy density; and
   administering HIFU to the ultrasound treatment site by the ultrasound transducer when the calculated ultrasound energy density is greater than or equal to the reference ultrasound energy density.

2. The method of claim 1, wherein the visual representation of the tissue is generated by receiving information from the HIFU transducer and wherein at least one image is generated from the received information.

3. The method of claim 1, wherein a plurality of ultrasound treatment sites are identified on the treatment region.

4. The method in claim 3, wherein calculating the ultrasound energy density for the proposed HIFU Treatment comprises the steps of:
   estimating an amount of energy to be deposited at each of the plurality of ultrasound treatment sites;
   summing the amount of energy to be deposited at each of the plurality of ultrasound treatment sites; and
   dividing the summed amount of energy to be deposited by one of a volume of the treatment region and a mass of the treatment region.

5. The method of claim 4, further comprising providing a visual cue on the monitor that the HIFU Treatment will be successful when the calculated ultrasound energy density is greater than or equal to the reference ultrasound energy density.

6. The method of claim 4, further comprising providing a visual cue on the monitor that the HIFU Treatment will not be successful when the calculated ultrasound energy density is less than the reference ultrasound energy density.

7. The method of claim 6, wherein an override option allows the proposed HIFU Treatment to progress even though the calculated ultrasound energy density is less than the reference ultrasound energy density.

8. The method of claim 1, further comprising providing a visual cue on the monitor that the proposed HIFU Treatment will be successful when the calculated ultrasound energy density is greater than or equal to the reference ultrasound energy density.

9. The method of claim 1, further comprising providing a visual cue on the monitor that the proposed HIFU Treatment will not be successful when the calculated ultrasound energy density is less than the reference ultrasound energy density.

10. The method of claim 9, wherein an override option allows the proposed HIFU Treatment to progress even though the calculated ultrasound energy density is less than the reference ultrasound energy density.

11. A method, implemented by a computing device, of providing treatment to a treatment region of tissue, the method comprising:
    providing a system comprising a monitor, a surgical tool having a ultrasound transducer, and a processor, the ultrasound transducer being configured to provide imaging of the treatment region and administer high intensity focused ultrasound ("HIFU") Treatment;
    positioning the ultrasound transducer proximate to tissue of the treatment region;

generating, by the computing device, a representation of the tissue;

identifying, by the computing device, an ultrasound treatment site on the treatment region from the representation of the tissue;

administering, by the computing device and the transducer, a HIFU Treatment to the ultrasound treatment site;

calculating, by the computing device, an ultrasound energy density for the HIFU Treatment, wherein the ultrasound energy density for the HIFU Treatment is calculated based on an amount of energy deposited into the ultrasound treatment site and an amount of energy planned to be deposited into the ultrasound treatment site; and comparing, by the computing device, the calculated ultrasound energy density for the HIFU Treatment to a reference ultrasound energy density.

12. The method of claim 11, wherein a plurality of ultrasound treatment sites are identified on the treatment region.

13. The method of claim 12, further comprising providing, by the computing device, a visual cue on the monitor that the HIFU Treatment will be successful when the calculated ultrasound energy density is greater than or equal to the reference ultrasound energy density.

14. The method of claim 12, further comprising providing, by the computing device, a visual cue on the monitor that the HIFU Treatment will not be successful when the calculated ultrasound energy density is less than the reference ultrasound energy density.

15. The method of claim 14, wherein an override option allows the HIFU Treatment to progress even though the calculated ultrasound energy density is less than the reference ultrasound energy density.

16. The method of claim 11 further, comprising providing, by the computing device, a visual cue on the monitor that the HIFU Treatment will be successful when the calculated ultrasound energy density is greater than or equal to the reference ultrasound energy density.

17. The method of claim 11, further comprising providing, by the computing device, a visual cue on the monitor that the HIFU Treatment will not be successful when the calculated ultrasound energy density is less than the reference ultrasound energy density.

18. The method of claim 17, wherein an override option allows the HIFU Treatment to progress even though the calculated ultrasound energy density is less than the reference ultrasound energy density.

\* \* \* \* \*